(12) United States Patent
Sudo et al.

(10) Patent No.: US 10,023,801 B2
(45) Date of Patent: *Jul. 17, 2018

(54) POLYMERIZABLE-COMPOUND-CONTAINING LIQUID CRYSTAL COMPOSITION AND LIQUID CRYSTAL DISPLAY ELEMENT USING SAME

(71) Applicant: DIC CORPORATION, Tokyo (JP)

(72) Inventors: Go Sudo, Kita-adachi-gun (JP); Shotaro Kawakami, Kita-adachi-gun (JP); Megumi Uzawa, Kita-adachi-gun (JP); Wei Wu, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/778,465

(22) PCT Filed: Feb. 21, 2014

(86) PCT No.: PCT/JP2014/054136
§ 371 (c)(1),
(2) Date: Sep. 18, 2015

(87) PCT Pub. No.: WO2014/148197
PCT Pub. Date: Sep. 25, 2014

(65) Prior Publication Data
US 2016/0289565 A1    Oct. 6, 2016

(30) Foreign Application Priority Data

Mar. 21, 2013   (JP) .................................. 2013-058131

(51) Int. Cl.
| G02F 1/1333 | (2006.01) |
| C09K 19/54 | (2006.01) |
| C07C 25/22 | (2006.01) |
| C09K 19/20 | (2006.01) |
| C09K 19/32 | (2006.01) |
| C09K 19/46 | (2006.01) |
| G02F 1/1337 | (2006.01) |
| C09K 19/34 | (2006.01) |
| C09K 19/04 | (2006.01) |
| C09K 19/30 | (2006.01) |

(52) U.S. Cl.
CPC ............ *C09K 19/542* (2013.01); *C07C 25/22* (2013.01); *C09K 19/20* (2013.01); *C09K 19/2007* (2013.01); *C09K 19/2014* (2013.01); *C09K 19/322* (2013.01); *C09K 19/3402* (2013.01); *C09K 19/46* (2013.01); *C09K 19/54* (2013.01); *G02F 1/133365* (2013.01); *G02F 1/133711* (2013.01); *C09K 2019/0448* (2013.01); *C09K 2019/0466* (2013.01); *C09K 2019/3027* (2013.01); *C09K 2019/3422* (2013.01); *C09K 2019/548* (2013.01)

(58) Field of Classification Search
CPC .. C09K 19/542; C09K 19/20; C09K 19/2007; C09K 19/2014; C09K 19/322; C09K 19/46; C09K 19/54; C09K 19/3402; C09K 2019/0448; C09K 2019/0466; C09K 2019/3027; C09K 2019/3422; C09K 2019/548; G02F 1/1333; G02F 1/13371; G02F 1/133365
USPC .............. 252/299.01, 299.6, 299.61; 428/1.1
See application file for complete search history.

(56) References Cited

U.S. PATENT DOCUMENTS

| 8,092,871 | B2 | 1/2012 | Usui et al. | |
| 8,603,358 | B2 * | 12/2013 | Kuriyama | C09K 19/2014 252/299.01 |
| 9,005,477 | B2 * | 4/2015 | Kuriyama | C09K 19/322 252/299.61 |
| 2012/0097895 | A1 | 4/2012 | Kuriyama et al. | |
| 2012/0292567 | A1 | 11/2012 | Kuriyama et al. | |
| 2015/0299570 | A1 * | 10/2015 | Kurisawa | C09K 19/2014 252/299.61 |
| 2016/0122650 | A1 * | 5/2016 | Hirata | G02F 1/133711 252/299.4 |

FOREIGN PATENT DOCUMENTS

| JP | 2012-18215 A | 1/2012 |
| JP | 2012-77200 A | 4/2012 |
| WO | 2010/119779 A1 | 10/2010 |
| WO | 2011/074384 A1 | 6/2011 |
| WO | 2013/022088 A1 | 2/2013 |

OTHER PUBLICATIONS

Internal Search Report dated May 27, 2014, issued in counterpart Application No. PCT/JP2014/054136 (2 pages).

* cited by examiner

*Primary Examiner* — Geraldina Visconti
(74) *Attorney, Agent, or Firm* — Westerman, Hattori, Daniels & Adrian, LLP

(57) ABSTRACT

There is provided a liquid crystal display device of a PSA type or the like that uses the polymerizable compound-containing liquid crystal composition, having a sufficiently fast response speed, capable of 3D displaying. Uniform and stable orientation control can be obtained at a lower energy cost. Provided are the polymerizable compound-containing liquid crystal composition containing one or two or more polymerizable compounds represented by general formula (M) as the first component, and containing one or two or more compounds represented by general formula (Na), general formula (Nb), or general formula (Nc) having a naphthalene unit as the second component. The liquid crystal display device uses the same.

20 Claims, No Drawings

POLYMERIZABLE-COMPOUND-CONTAINING LIQUID CRYSTAL COMPOSITION AND LIQUID CRYSTAL DISPLAY ELEMENT USING SAME

TECHNICAL FIELD

The present invention relates to a polymerizable compound-containing liquid crystal composition and a liquid crystal display device using the same.

BACKGROUND ART

A PSA (Polymer Sustained Alignment) type liquid crystal display device has a polymer structure formed in a cell in order to control a pretilt angle of a liquid crystal molecule, and has been practically used as a next-generation liquid crystal display device due to the characteristics of high-speed responsiveness, high contrast, and the like.

The PSA type liquid crystal display device is a liquid crystal display device using a polymerizable compound-containing liquid crystal composition including a liquid crystal compound and a polymerizable compound, and is manufactured by polymerizing the polymerizable compound in a state where liquid crystal molecules are aligned by applying a voltage so as to fix the alignment of the liquid crystal molecules. In the process of polymerizing the polymerizable compound of the PSA type liquid crystal display device, the polymerization reaction rate of the polymerizable compound is very important for productivity. The adjustment of a pretilt angle influencing the response speed and contrast of the PSA type liquid crystal display device, or the adjustment of the residual amount of the polymerizable compound influencing reliability such as display unevenness or image persistence is also very important. Since the polymerization reaction rate of the polymerizable compound depends on the wavelength and irradiation intensity of an UV irradiation lamp, it has been required to develop a polymerizable compound-containing liquid crystal composition containing a polymerizable compound met specifications of the UV irradiation lamp. However, sufficient support has been difficult.

As an approach from a liquid crystal composition, there is introduced a technology of reducing a polymerization reaction rate by containing a liquid crystal compound having a terphenyl ring (PTL 1). However, when the liquid crystal compound having a terphenyl ring is used, it may make an influence on reliability such as display unevenness or image persistence due to a decrease in VHR.

As described above, a polymerizable compound-containing liquid crystal composition satisfying the adjustment of the polymerization reaction rate adapted for the UV irradiation lamp, the high-speed responsiveness and high contrast of a liquid crystal display device, and the display unevenness and image persistence of a liquid crystal display device has been required, and a liquid crystal display device using the polymerizable compound-containing liquid crystal composition has also been required.

CITATION LIST

Patent Literature

[PTL 1] U.S. Pat. No. 8,092,871

SUMMARY OF INVENTION

Technical Problem

An object of the present invention is to provide a polymerizable compound-containing liquid crystal composition that has a sufficiently low viscosity ($\eta$), a sufficiently low rotational viscosity ($\gamma 1$), a sufficiently fast reaction speed of a polymerizable compound, and a lack of or a sufficiently suppressed amount of residual polymerizable compound after UV irradiation. Further, another object is to provide a PSA type liquid crystal display device that uses the polymerizable compound-containing liquid crystal composition, has a sufficiently fast response speed, is capable of 3D display, and is configured such that uniform and stable orientation control is obtained at a lower energy cost.

Solution to Problem

The present inventors have investigated various polymerizable compounds and liquid crystal compounds. As a result, they found that a polymerizable compound-containing liquid crystal composition including a polymerizable compound having a specific structure and a liquid crystal compound having a specific structure can solve the above-described problem, thereby completing the present invention.

That is, the present invention provides a polymerizable compound-containing liquid crystal composition, including: one or two or more kinds of polymerizable compounds represented by general formula (M), as a first component; and

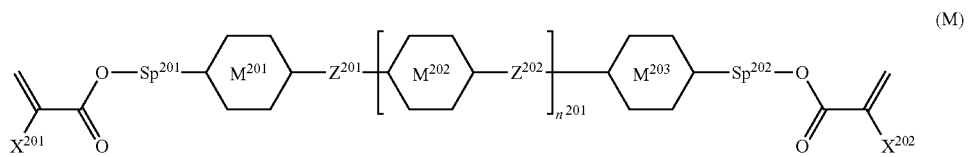

(M)

one or two or more kinds of compounds having a naphthalene unit, represented by general formula (Na), general formula (Nb), or general formula (Nc), as a second component.

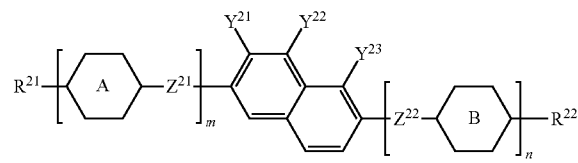

(Na)

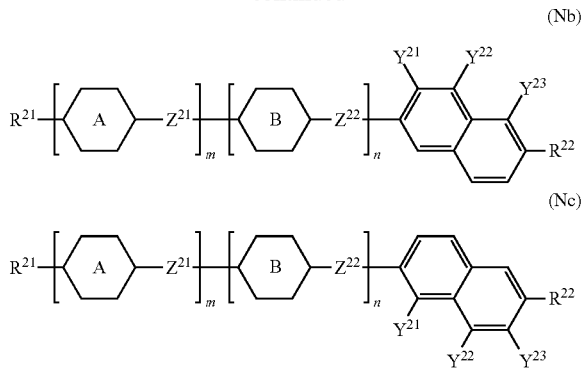

Further, the present invention provides a liquid crystal display device using the polymerizable compound-containing liquid crystal composition, and a compound represented by general formula (Na), general formula (Nb), or general formula (Nc).

Advantageous Effects of Invention

Since the polymerizable compound-containing liquid crystal composition of the present invention has a sufficiently low viscosity (η), the liquid crystal display device using the polymerizable compound-containing liquid crystal composition has a sufficiently fast response speed, and is capable of 3D display. Further, since the polymerizable compound does not remain or the residual amount thereof is sufficiently suppressed, display unevenness or image persistence does not occur or is extremely suppressed. Furthermore, since the polymerization reaction speed of the polymerizable compound is sufficiently fast, an energy cost for production can be reduced to improve the production efficiency, and uniform and stable orientation control can be obtained. Therefore, the polymerizable compound-containing liquid crystal composition of the present invention is very useful.

DESCRIPTION OF EMBODIMENTS

The polymerizable compound-containing liquid crystal composition of the present invention includes one or two or more kinds of polymerizable compounds represented by general formula (M), as a first component.

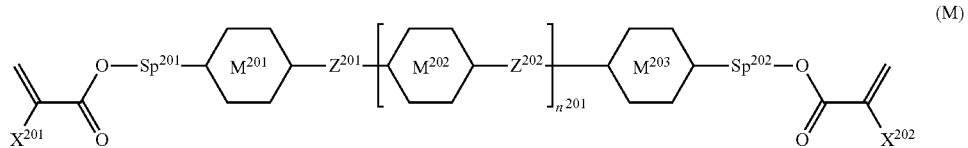

In general formula (M), $X^{201}$ and $X^{202}$ each independently represent a hydrogen atom, a methyl group, or a $-CF_3$ group. The polymerizable compound is preferably a diacrylate derivative in which both $X^{201}$ and $X^{202}$ are hydrogen atoms or a dimethacrylate derivative in which both $X^{201}$ and $X^{202}$ are methyl groups, and is also preferably a compound in which one of $X^{201}$ and $X^{202}$ is a hydrogen atom and the other thereof is a methyl group. It is possible to use a preferable compound according to application, but, in a PSA display device, it is preferable that the polymerizable compound represented by general formula (M) has at least one methacrylate derivative, and it is also preferable that polymerizable compound represented by general formula (M) has two methacrylate derivatives.

$Sp^{201}$ and $Sp^{202}$ each independently represent a single bond, an alkylene group having 1 to 8 carbon atoms, or $-O-(CH_2)_s-$ (provided that, in the formula, s represents an integer of 2 to 7, and oxygen atom is bonded to a ring). In a PSA mode liquid crystal display device, it is preferable that at least one of $Sp^{201}$ and $Sp^{202}$ is a single bond, and it is preferable that both $Sp^{201}$ and $Sp^{202}$ are single bonds, or one of $Sp^{201}$ and $Sp^{202}$ is a single bond and the other of $Sp^{201}$ and $Sp^{202}$ is an alkylene group having 1 to 8 carbon atoms or $-O-(CH_2)_s-$. In this case, it is preferable that an alkylene group having 1 to 4 carbon atoms is used, and it is preferable that s is 1 to 4.

Ring $M^{201}$, ring $M^{202}$, and ring $M^{203}$ each independently represent a trans-1,4-cyclohexylene group (one $-CH_2-$ or non-adjacent two or more $-CH_2-$ in the group may be substituted with $-O-$ or $-S-$), a 1,4-phenylene group (one $-CH=$ or non-adjacent two or more $-CH=$ in the group may be substituted with $-N=$), a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group. Hydrogen atoms in the group each independently may be substituted with a fluorine atom, a $-CF_3$ group, an alkyl group having 1 to 10 carbon atoms, an alkoxy group having 1 to 10 carbon atoms, or any of formulae (R-1) to (R-15).

(R-1)

(R-2)

(R-3)

-continued

(R-4)

(R-5)

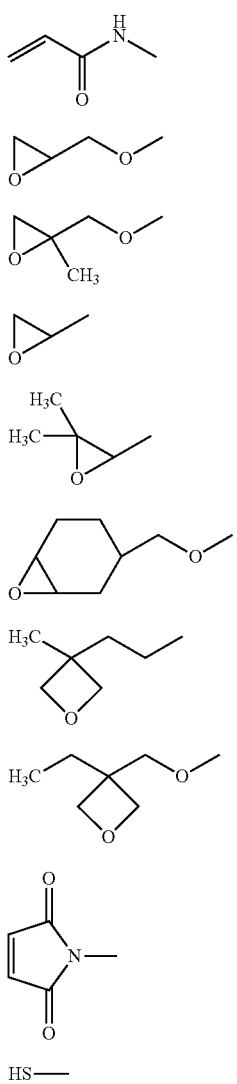

(R-6)
(R-7)
(R-8)
(R-9)
(R-10)
(R-11)
(R-12)
(R-13)
(R14)
(R-15)

$Z^{201}$ and $Z^{202}$ each independently represents —OCH$_2$—, —CH$_2$O—, —COO—, —OCO—, —CF$_2$O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CY$^1$=CY$^2$— (in the formula, Y$^1$ and Y$^2$ each independently represent a fluorine atom or a hydrogen atom), —C≡C—, or a single bond, preferably —COO—, —OCO—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —C≡C—, or a single bond, and more preferably, —COO—, —OCO—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, or a single bond.

$n^{201}$ represents 0, 1, or 2, preferably 0 or 1. However, when ring $M^{202}$ and $Z^{202}$ plurally exist, respectively, they may be different from each other or the same as each other, respectively.

The polymerizable compound-containing liquid crystal composition of the present invention includes at least one kind of polymerizable compound represented by general formula (M), preferably one to five kinds of polymerizable compounds, and more preferably one to three kinds of polymerizable compounds. When the content of the polymerizable compound represented by general formula (M) is small, alignment regulating force to the liquid crystal composition is weakened. In contrast, when the content of the polymerizable compound represented by general formula (M) is too large, energy required at the time of polymerization is increased, and the amount of the polymerizable compound remaining without being polymerized is increased, so as to cause a display defect. Therefore, the content thereof is preferably 0.01 mass % to 2.00 mass %, more preferably 0.05 mass % to 1.00 mass %, and particularly preferably 0.10 mass % to 0.50 mass %.

More specifically, when $n^{201}$ is 0 in general formula (M), ring structures between $Sp^{201}$ and $Sp^{202}$ are preferably formulae (XXa-1) to (XXa-5), more preferably formulae (XXa-1) to (XXa-3), and particularly preferably formulae (XXa-1) or (XXa-2). Provided that, both ends of the formula shall be bound to $Sp^{221}$ or $Sp^{202}$.

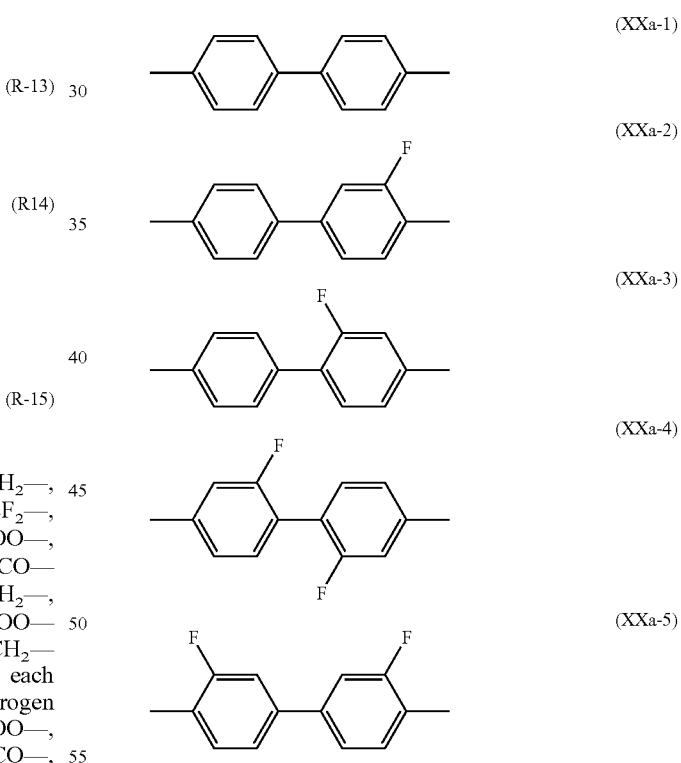

(XXa-1)
(XXa-2)
(XXa-3)
(XXa-4)
(XXa-5)

In the polymerizable compounds having these skeletons, represented by general formula (M), alignment regulating force after polymerization is most suitable for a PSA mode liquid crystal display device, and a good alignment state is obtained. Therefore, there is an effect of display unevenness being suppressed or not occurring at all.

From the above, as a polymerizable monomer, a compound represented by any one of formulae (XX-1) to (XX-10) is preferable, and a compound represented by any one of formulae (XX-1) to (XX-4) is more preferable.

(XX-1)
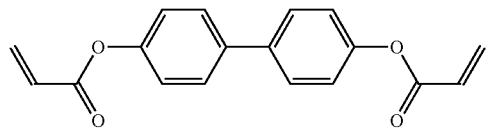

(XX-2)
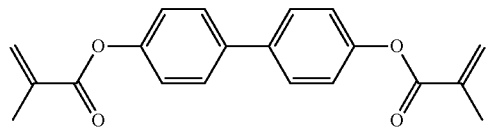

(XX-3)
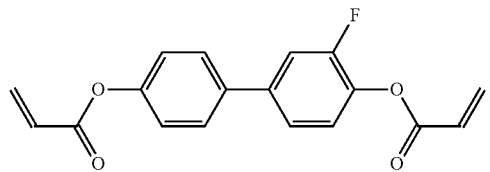

(XX-4)
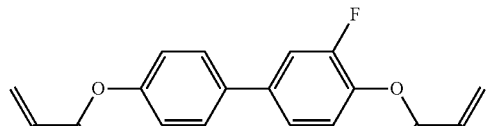

(XX-5)
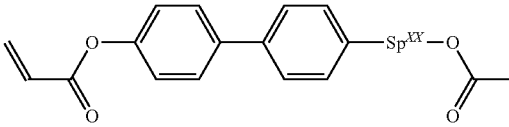

(XX-6)
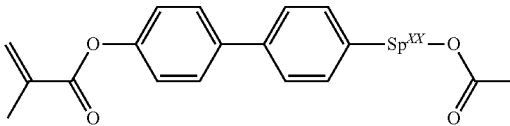

(XX-7)
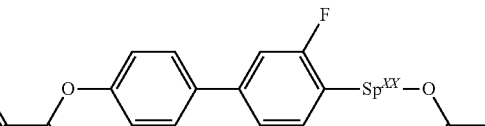

(XX-8)
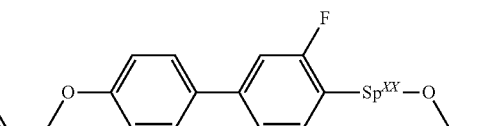

(XX-9)

(XX-10)
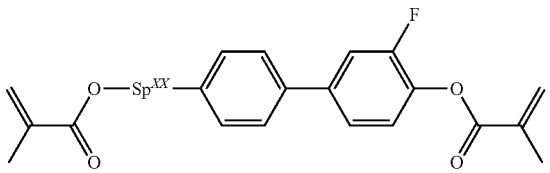

In the formulae, $Sp^{xx}$ represents an alkylene group having 1 to 8 carbon atoms or —O—$(CH_2)_s$— (provided that, in the formula, s is an integer of 2 to 7, and an oxygen atom is bonded to a ring).

The hydrogen atom in the phenyl group in the formula may be substituted with —F, —Cl, —$CF_3$, —$CH_3$, or any one of formulae (R-1) to (R-15)

When $n^{201}$ is 1 in general formula (M), for example, polymerizable compounds represented by formulae (M31) to (M48) are preferable.

(M31)
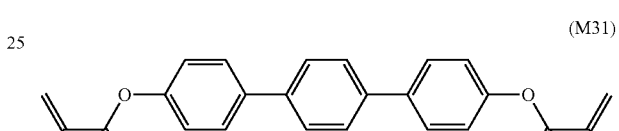

(M32)
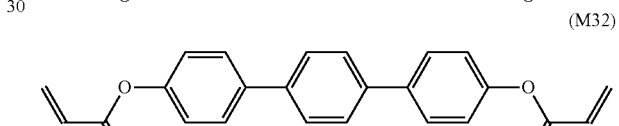

(M33)

(M34)
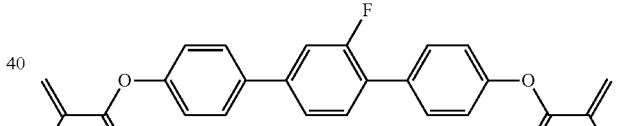

(M35)
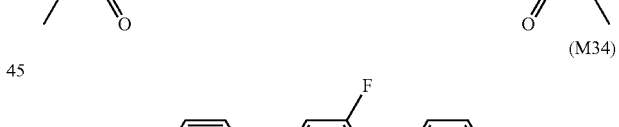

(M36)
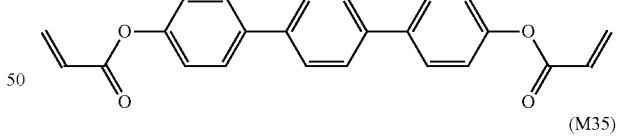

(M37) 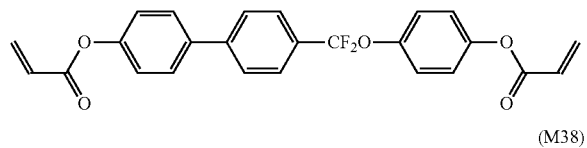

(M38) 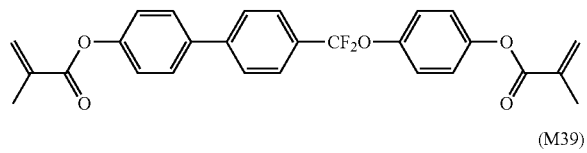

(M39) 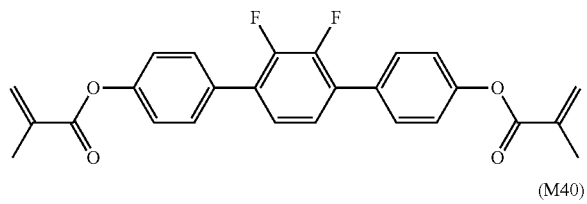

(M40) 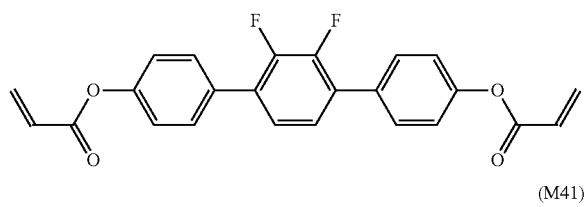

(M41) 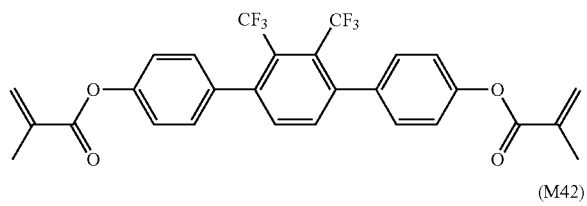

(M42) 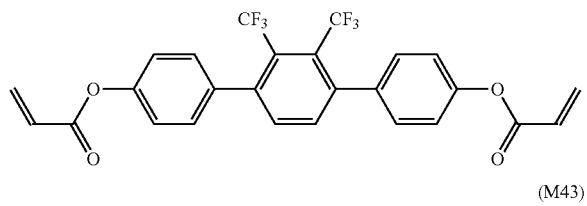

(M43) 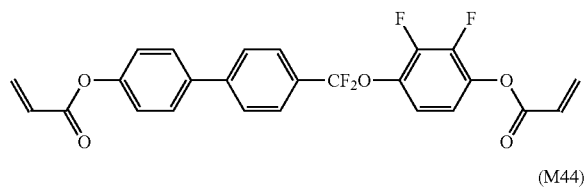

(M44) 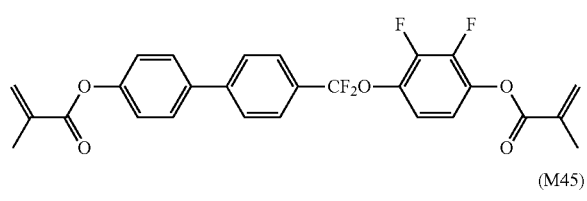

(M45) 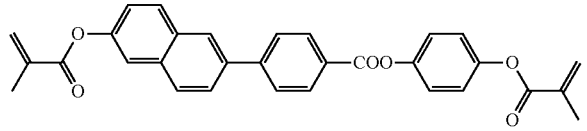

(M46) 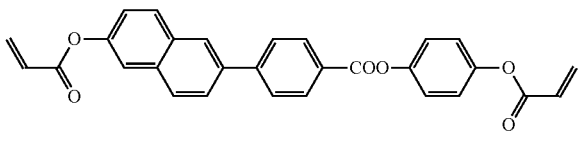

(M47) 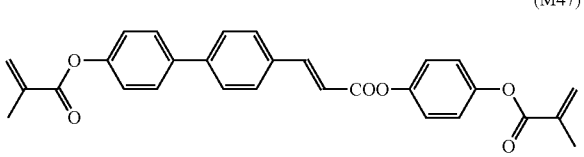

(M48) 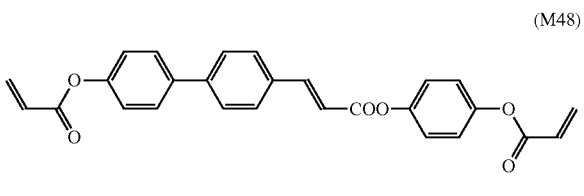

Each of the hydrogen atoms in the phenyl group and the naphthalene group in the formula may be substituted with —F, —Cl, —CF$_3$, —CH$_3$, or any one of formulae (R-1) to (R-15)

In the polymerizable compounds having these skeletons, represented by general formula (M), alignment regulating force after polymerization is most suitable for a PSA mode liquid crystal display device, and a good alignment state is obtained. Therefore, there is an effect of display unevenness being suppressed or not occurring at all.

When $n^{201}$ is 1 in general formula (M) and a plurality of formulae (R-1) or formulae (R-2) exist in general formula (M), for example, polymerizable compounds represented by formulae (M301) to (M316) are preferable.

(M301) 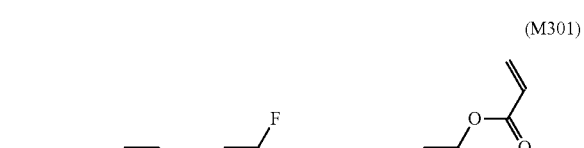

(M302) 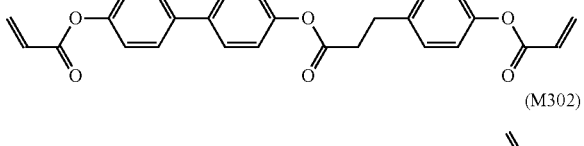

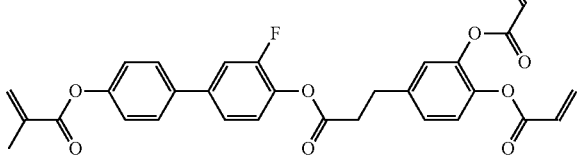

(M303) 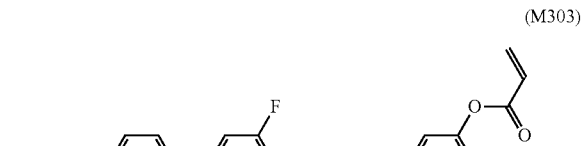

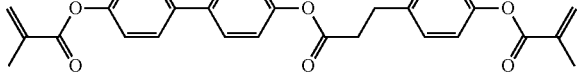

(M304)
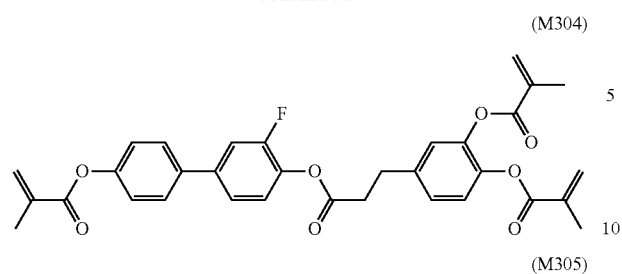

(M305)
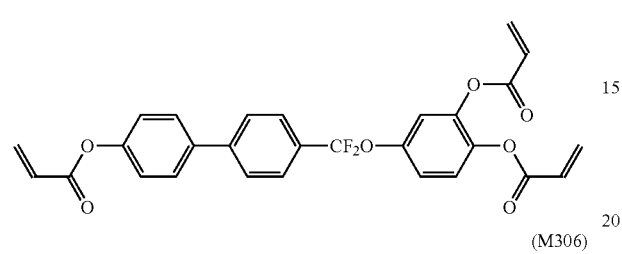

(M306)
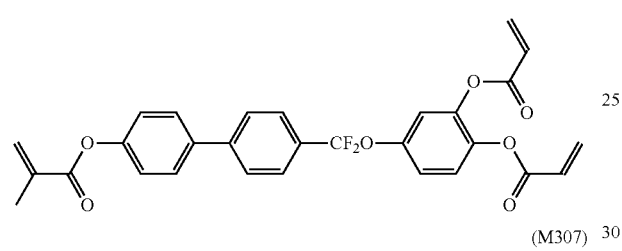

(M307)
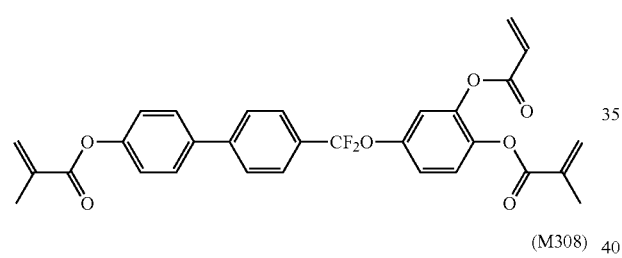

(M308)
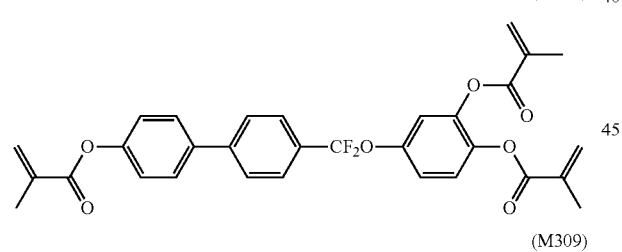

(M309)
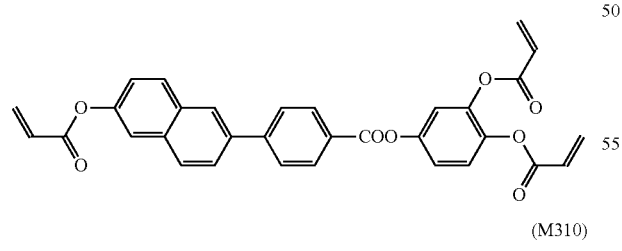

(M310)
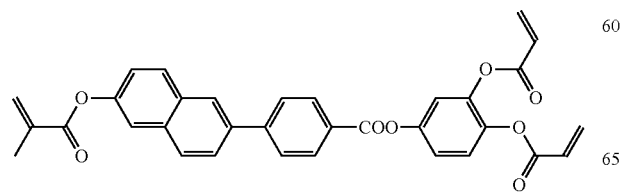

(M311)
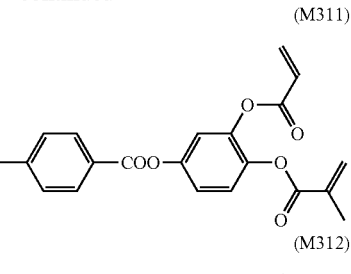

(M312)
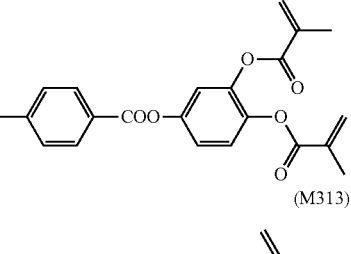

(M313)
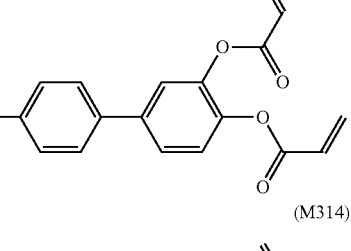

(M314)
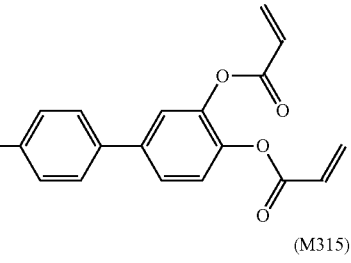

(M315)
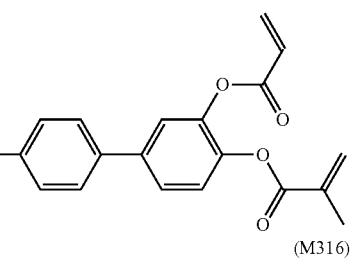

(M316)
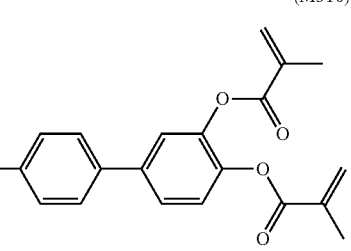

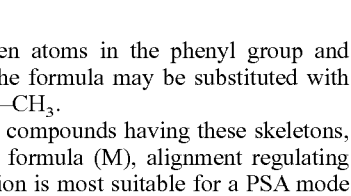

Each of the hydrogen atoms in the phenyl group and naphthalene group in the formula may be substituted with —F, —Cl, —CF$_3$, or —CH$_3$.

In the polymerizable compounds having these skeletons, represented by general formula (M), alignment regulating force after polymerization is most suitable for a PSA mode liquid crystal display device, and a good alignment state is obtained. Therefore, there is an effect of display unevenness being suppressed or not occurring at all.

The polymerizable compound-containing liquid crystal composition of the present invention includes one or two or more kinds of compounds having a naphthalene unit, which are selected from the group consisting of liquid crystal compounds represented by general formula (Na), general formula (Nb), or general formula (Nc), as a second component.

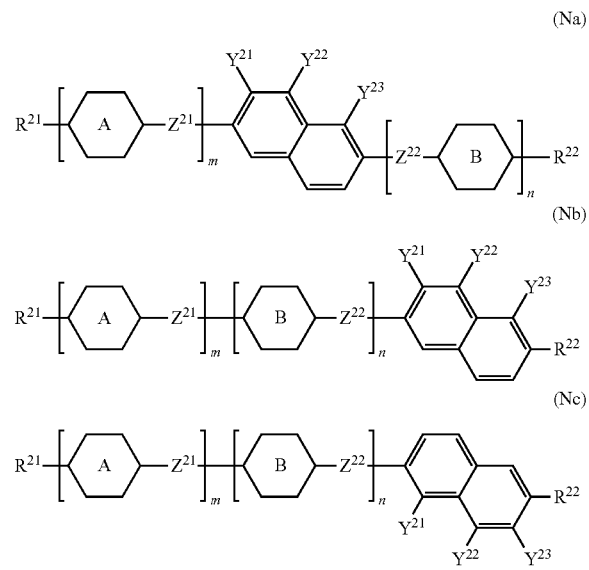

In general formula (Na), general formula (Nb), or general formula (Nc), $R^{21}$ or $R^{22}$ represents an alkyl group having 1 to 10 carbon atoms, an alkoxy group having 1 to 10 carbon atoms, an alkenyl group having 2 to 10 carbon atoms, or an alkenyloxy group having 2 to 10 carbon atoms. One or two or more hydrogen atoms existing in these groups may be substituted with fluorine atoms. $R^{21}$ is more preferably a linear alkyl group having 1 to 5 carbon atoms or a linear alkenyl group having 2 to 5 carbon atoms, and particularly preferably an alkyl group having 1 to 5 carbon atoms. $R^{22}$ is more preferably a linear alkyl group having 1 to 5 carbon atoms, a linear alkoxy group having 1 to 5 carbon atoms, or a linear alkenyl group having 2 to 5 carbon atoms, and particularly preferably an alkoxy group having 1 to 5 carbon atoms.

$Y^{21}$ to $Y^{23}$ each independently represent a hydrogen atom, a methyl group, a —$CF_3$ group, a fluorine atom, or a chlorine atom, and more preferably a hydrogen atom or a fluorine atom.

Ring A and ring B each independently represent a trans-1,4-cyclohexylene group (one —$CH_2$— or two or more non-adjacent —$CH_2$— in the group may be substituted with —O— or —S—), a 1,4-phenylene group (one —CH= or two or more non-adjacent —CH= in the group may be substituted with —N=), a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, more preferably a trans-1,4-cyclohexylene group, a 1,4-phenylene group, a 2-fluoro-1,4-phenylene group, a 3-fluoro-1,4-phenylene group, a 3,5-difluoro-1,4-phenylene group, or a 2,3-difluoro-1,4-phenylene group, and particularly preferably a trans-1,4-cyclohexylene group or a 1,4-phenylene group.

$Z^{21}$ and $Z^{22}$ each independently represent —$OCH_2$—, —$CH_2O$—, —COO—, —OCO—, —$CF_2O$—, —$OCF_2$—, —$CH_2CH_2$—, —$CF_2CF_2$—, —C≡C—, or a single bond.

m represents 0, 1, or 2, preferably 0 or 1. However, when ring A and $Z^{21}$ plurally exist, respectively, they may be different from each other or the same as each other, respectively.

n represents 0, 1, or 2, preferably 0 or 1. However, when ring B and $Z^{22}$ plurally exist, respectively, they may be different from each other or the same as each other, respectively.

m+n is preferably 1 or more, more preferably 1 or 2, and particularly preferably 2.

The polymerizable compound-containing liquid crystal composition of the present invention includes one or two or more kinds of compounds selected from the group consisting of compounds represented by general formula (Na), general formula (Nb), or general formula (Nc), preferably one to five kinds of compounds, more preferably one to three kinds of compounds, and particularly preferably one kind of compound. The content of the compound is 0.5 mass % to 50 mass %, preferably 0.5 mass % to 10 mass %, more preferably 0.5 mass % to 5 mass %, and particularly preferably 0.5 mass % to 4 mass %. The content thereof may be 0.5 mass % to 3 mass %, and may also be 0.5 mass % to 2 mass %.

More specifically, the compounds selected from the group consisting of compounds represented by general formula (Na), general formula (Nb), or general formula (Nc) are preferably compounds represented by general formulae (N-001) to (N-109)

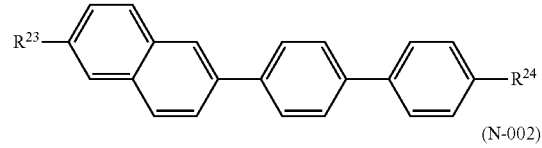

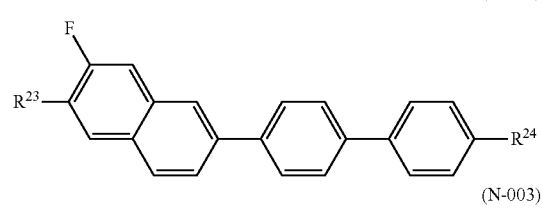

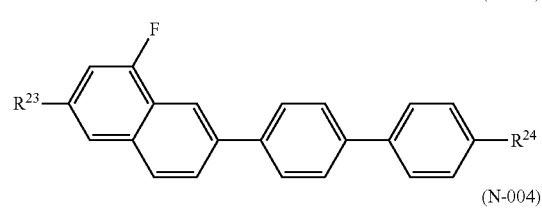

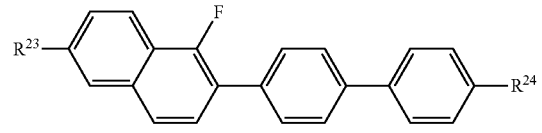

(N-005) 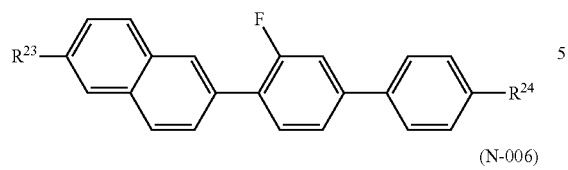
(N-006) 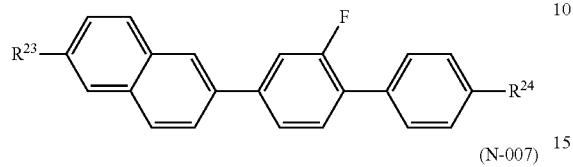
(N-007) 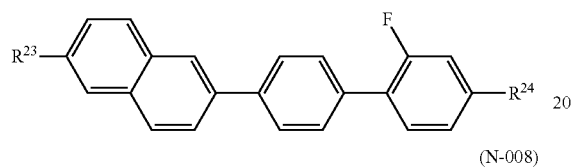
(N-008) 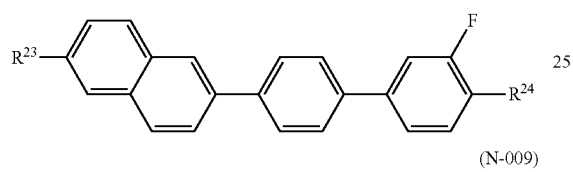
(N-009) 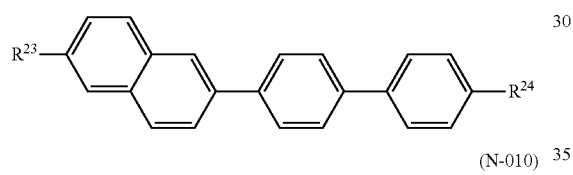
(N-010) 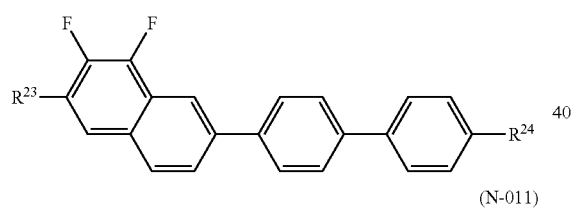
(N-011) 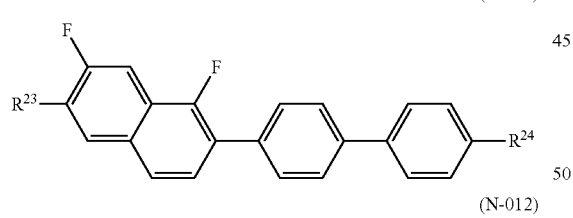
(N-012) 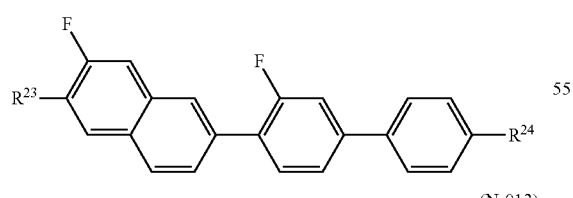
(N-013) 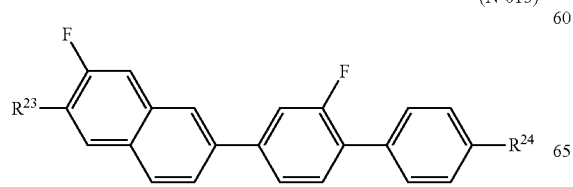
(N-014) 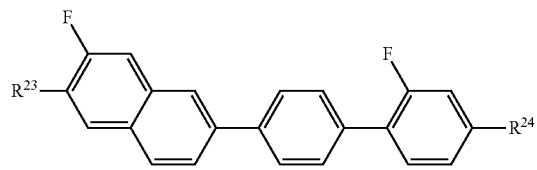
(N-015) 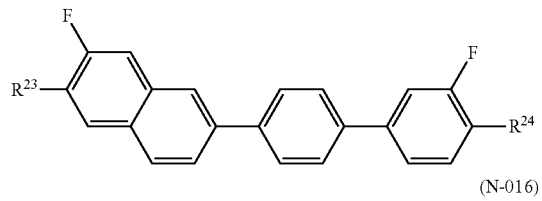
(N-016) 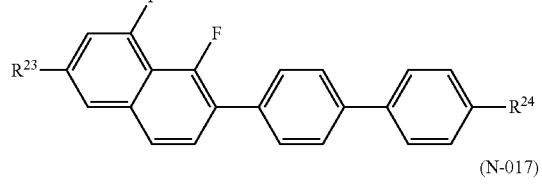
(N-017) 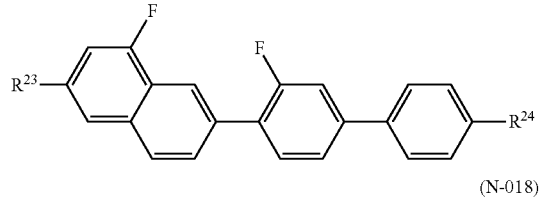
(N-018) 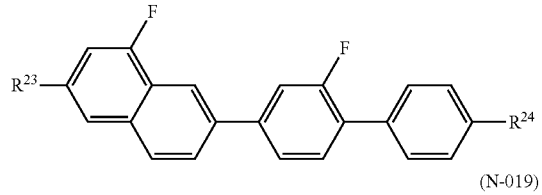
(N-019) 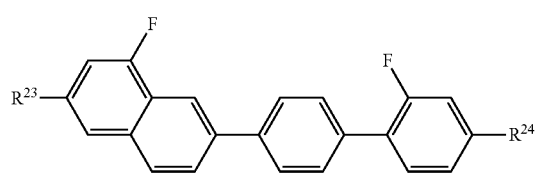
(N-020) 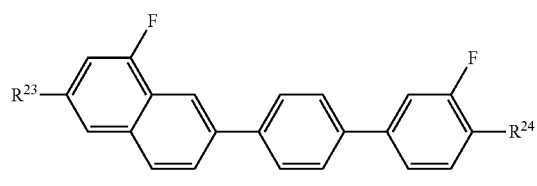
(N-021) 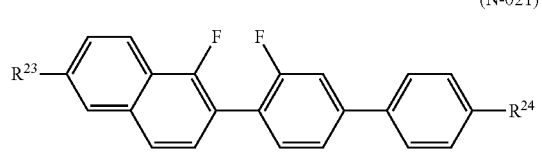

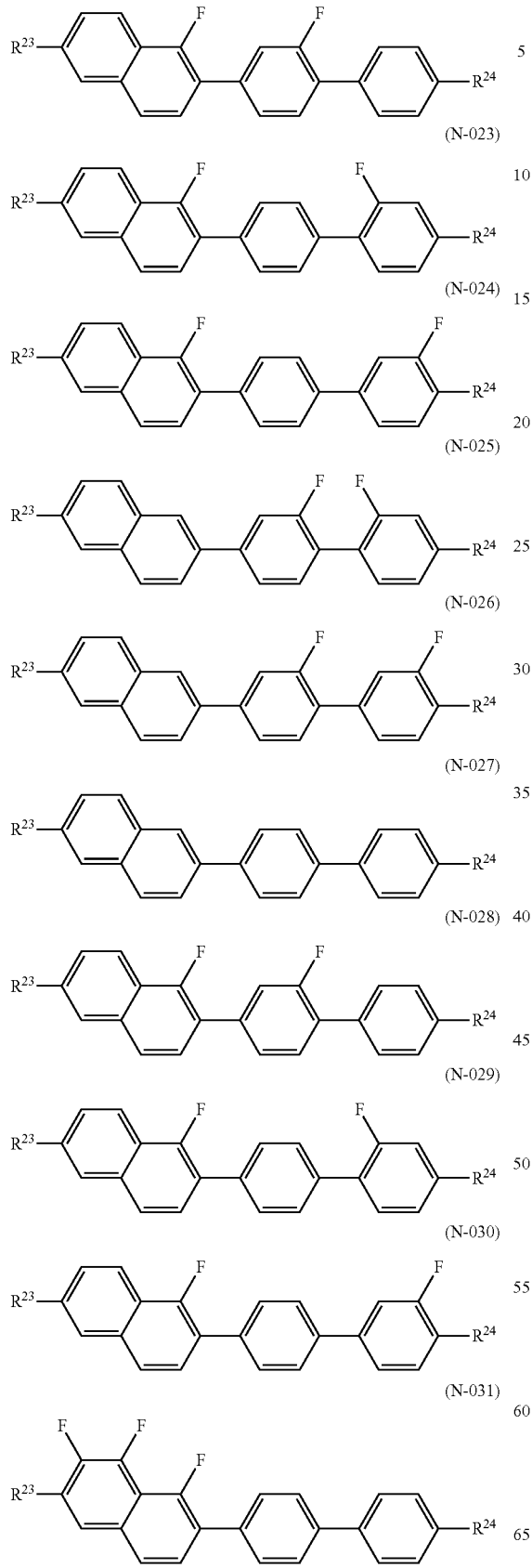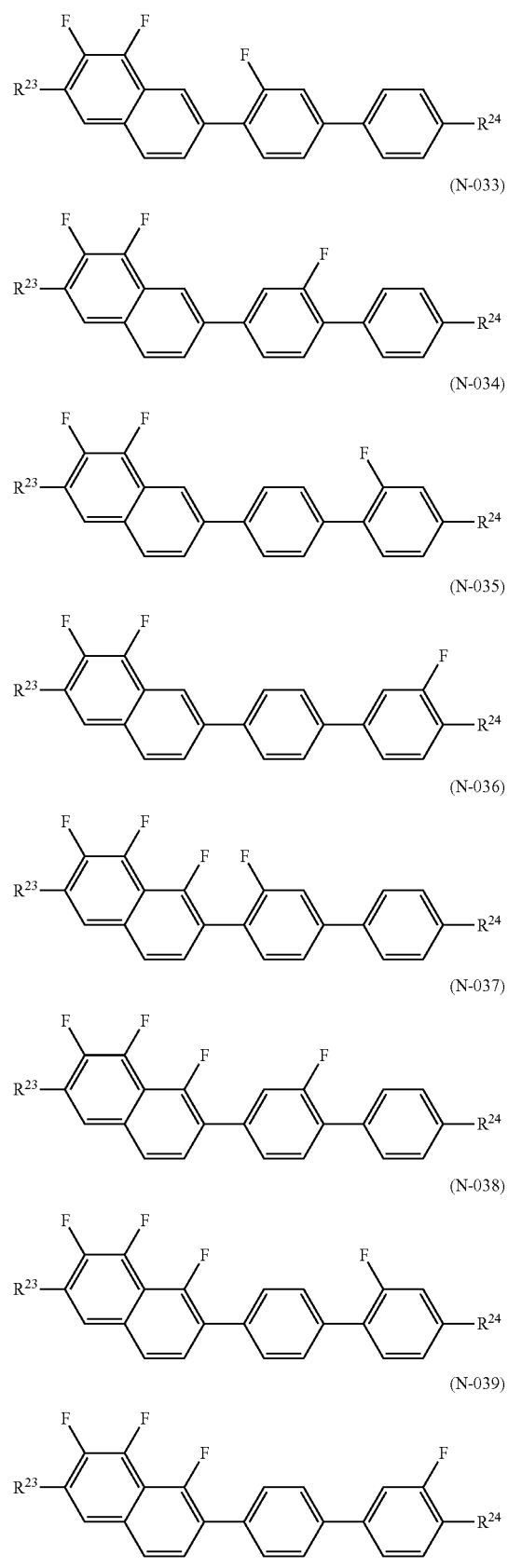

(N-040) through (N-056): chemical structure diagrams.

(N-057)
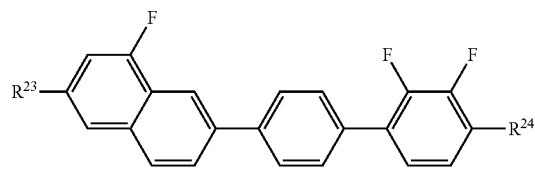
(N-058)
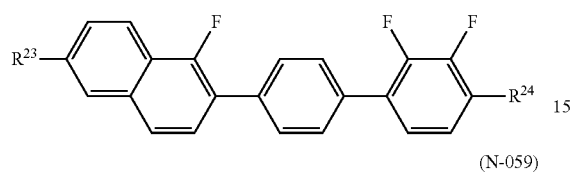
(N-059)
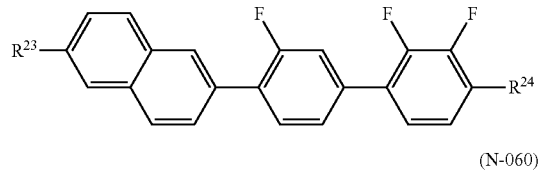
(N-060)
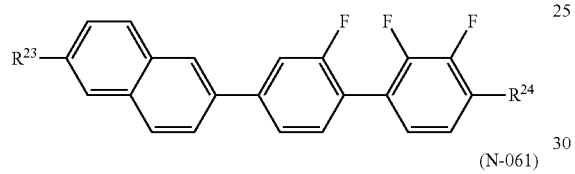
(N-061)
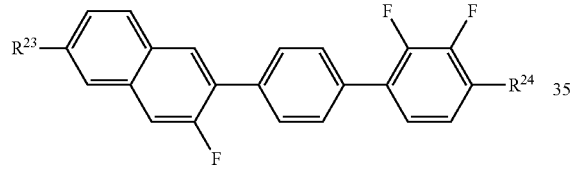
(N-062)
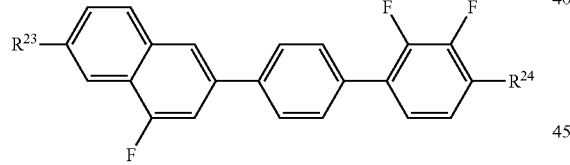
(N-063)
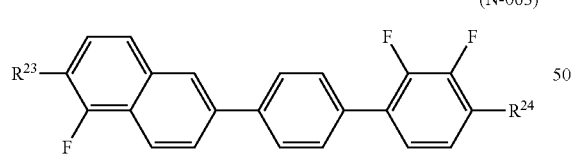
(N-064)
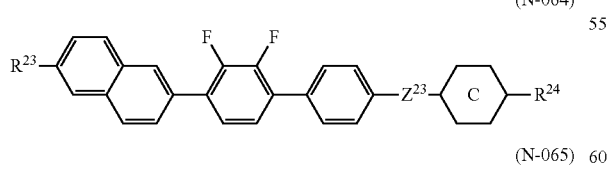
(N-065)
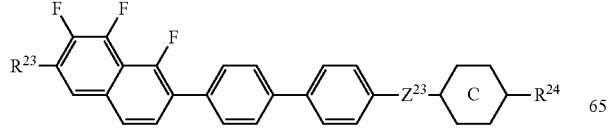
(N-066)
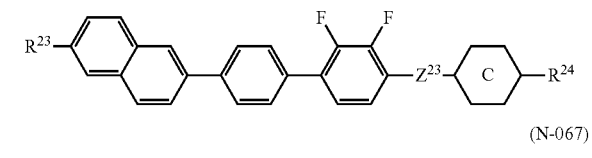
(N-067)
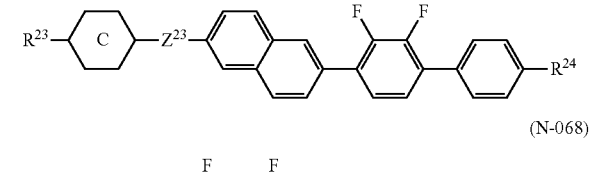
(N-068)
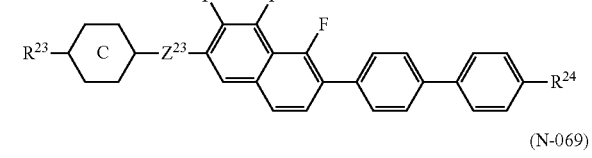
(N-069)
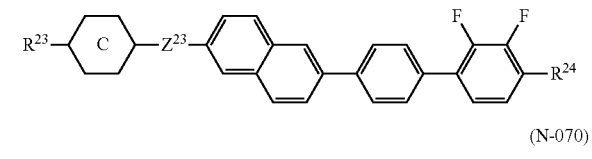
(N-070)
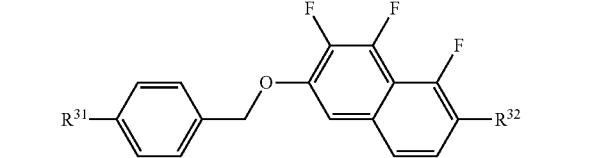
(N-071)
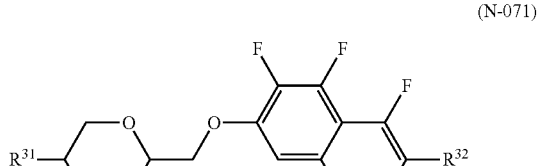
(N-072)
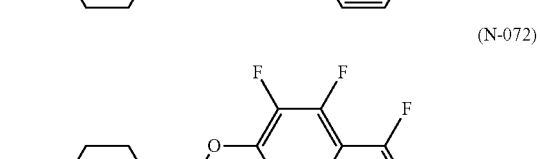
(N-073)
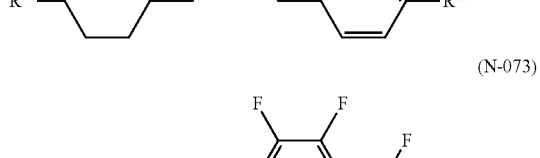
(N-074)
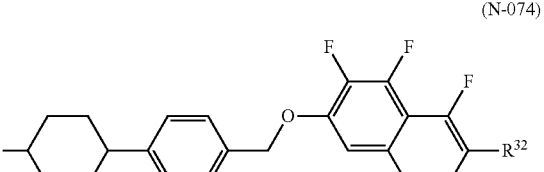

(N-075)
(N-076)
(N-077)
(N-078)
(N-079)
(N-080)
(N-081)
(N-082)
(N-083)
(N-084)
(N-085)
(N-086)
(N-087)
(N-088)
(N-089)
(N-090)

(N-091)
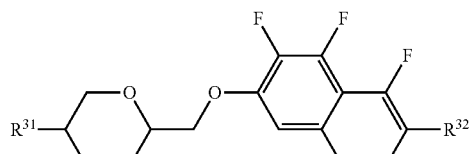
(N-092)
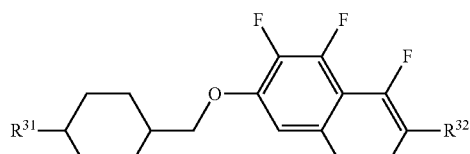
(N-093)
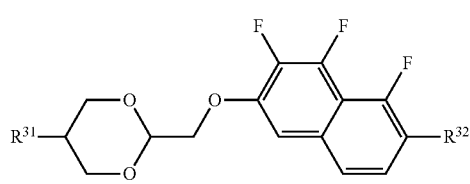
(N-094)
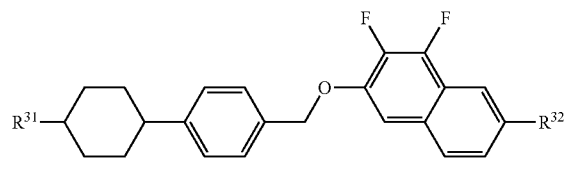
(N-095)
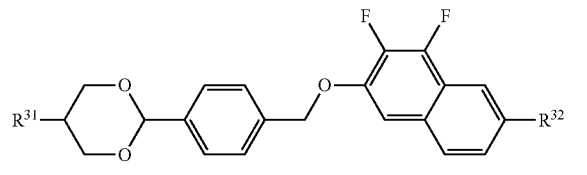
(N-096)
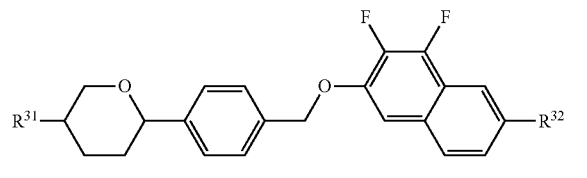
(N-097)
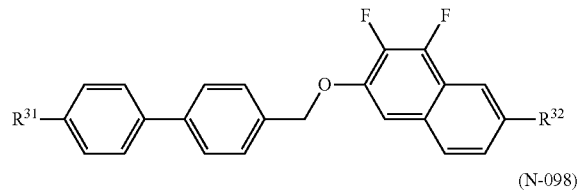
(N-098)
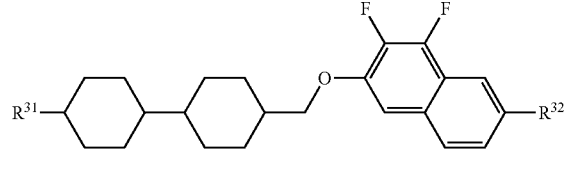
(N-099)
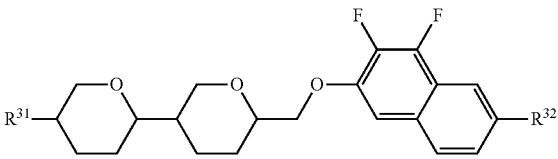
(N-100)
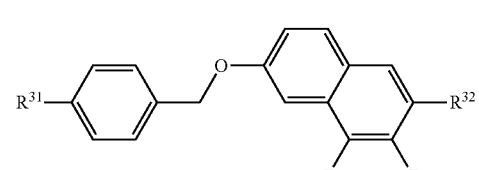
(N-101)
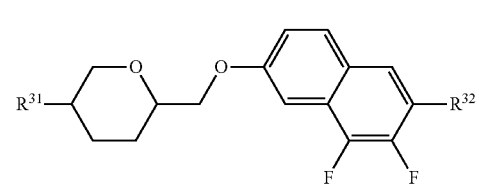
(N-102)
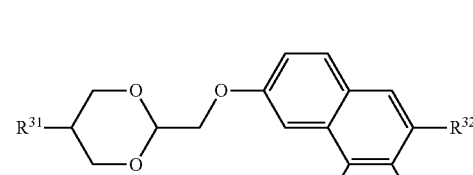
(N-103)
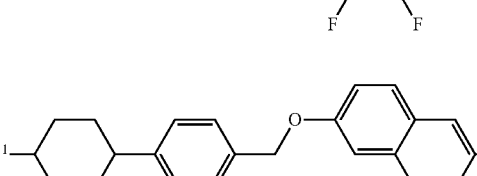
(N-104)
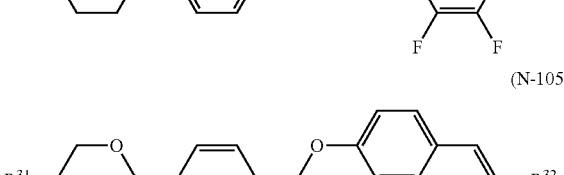
(N-105)
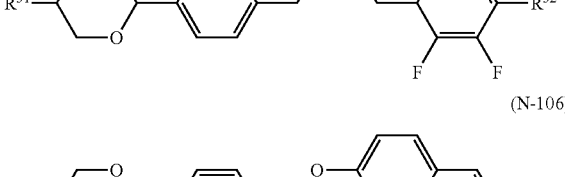
(N-106)
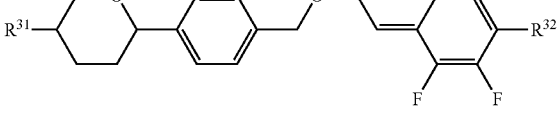

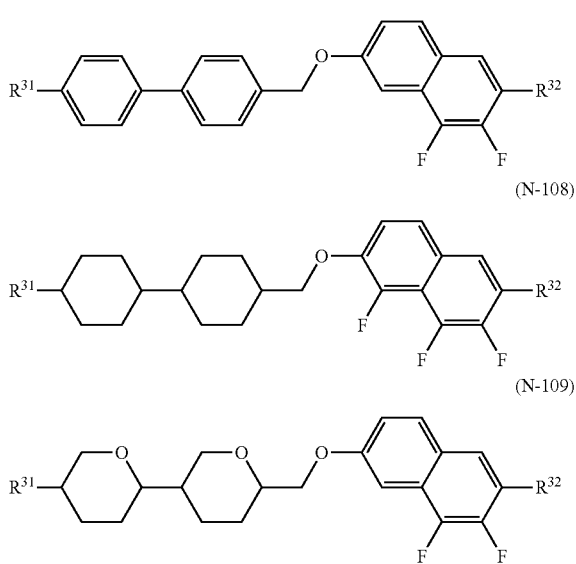

In the formulae, $R^{23}$ and $R^{31}$ each independently represent the same meaning as $R^{21}$; $R^{24}$ and $R^{32}$ each independently represent the same meaning as $R^{22}$; $Z^{23}$ represents a single bond, —CH$_2$—O—, —O—CH$_2$—, —CF$_2$—O—, —O—CF$_2$—, —CH$_2$CH$_2$—, or —CF$_2$CF$_2$—; and ring C represents trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group. Further, in the formulae, each of the hydrogen atoms in the phenyl group and the naphthalene group may be substituted with any of —F, —Cl, —CF$_3$, and —CH$_3$.

Among the compounds represented by general formulae (N-001) to (N-019), the compounds represented by general formulae (N-001) to (N-009) are preferable, the compounds represented by general formulae (N-001) to (N-003) are more preferable, and the compound represented by general formula (N-001) is particularly preferable.

The polymerizable compound-containing liquid crystal composition of the present invention further includes one or two or more kinds of compounds represented by general formula (II), preferably one to ten kinds of compounds, and more preferably one to five kinds of compounds. The content thereof is 10 mass % to 90 mass %, more preferably 10 mass % to 70 mass %, and particularly preferably 20 mass % to 50 mass %.

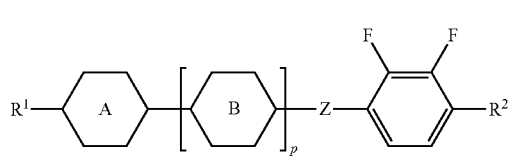

In the formula, $R^1$ and $R^2$ each independently represent an alkyl group having 1 to 10 carbon atoms, an alkoxy group having 1 to 10 carbon atoms, an alkenyl group having 2 to 10 carbon atoms, or an alkenyloxy group having 2 to 10 carbon atoms. One —CH$_2$— or two or more non-adjacent —CH$_2$— existing in $R^1$ and $R^2$ each independently may be substituted with —O— or —S—. Further, one hydrogen atom or two or more hydrogen atoms existing in $R^1$ and $R^2$ each independently may be substituted with a fluorine atom or a chlorine atom. $R^1$ and $R^2$ each independently represent more preferably a linear alkyl group having 1 to 5 carbon atoms, a linear alkoxy group having 1 to 5 carbon atoms, an alkenyl group having 2 to 5 carbon atoms, or an alkenyloxy group having 2 to 5 carbon atoms. $R^1$ is particularly preferably an alkyl group having 1 to 5 carbon atoms or an alkenyl group having 2 to 5 carbon atoms. $R^2$ is particularly preferably an alkoxy group having 1 to 5 carbon atoms.

Ring A and ring B represent the same meaning as that described above.

p represents 0, 1, or 2, more preferably 0 or 1.

Z represents —OCH$_2$—, —CH$_2$O—, —CF$_2$O—, —OCF$_2$—, —CH$_2$CH$_2$—, —CF$_2$CF$_2$—, — or a single bond, more preferably —CH$_2$O—, —CF$_2$O—, —CH$_2$CH$_2$—, or a single bond, and particularly preferably —CH$_2$O— or a single bond.

The compound represented by general formula (II) is preferably compounds represented by general formulae (II-A1) to (II-A5) and general formulae (II-B1) to (II-B5), more preferably compounds represented by general formulae (II-A1) to (II-A5), and particularly preferably a compound represented by general formula (II-A1) or (II-A3)

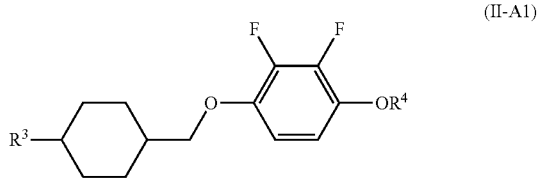

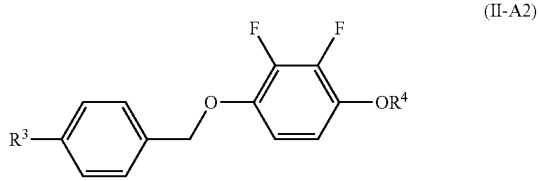

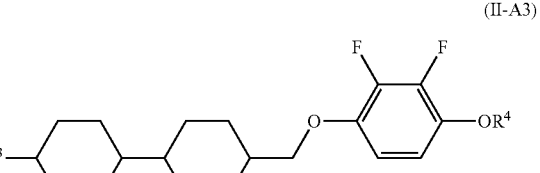

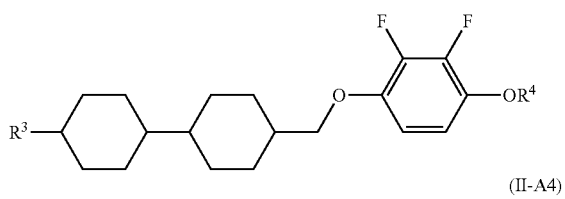

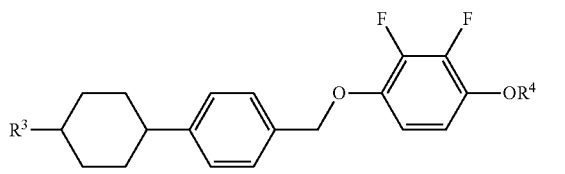

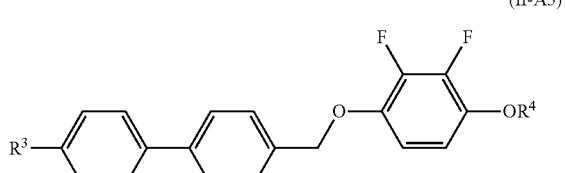

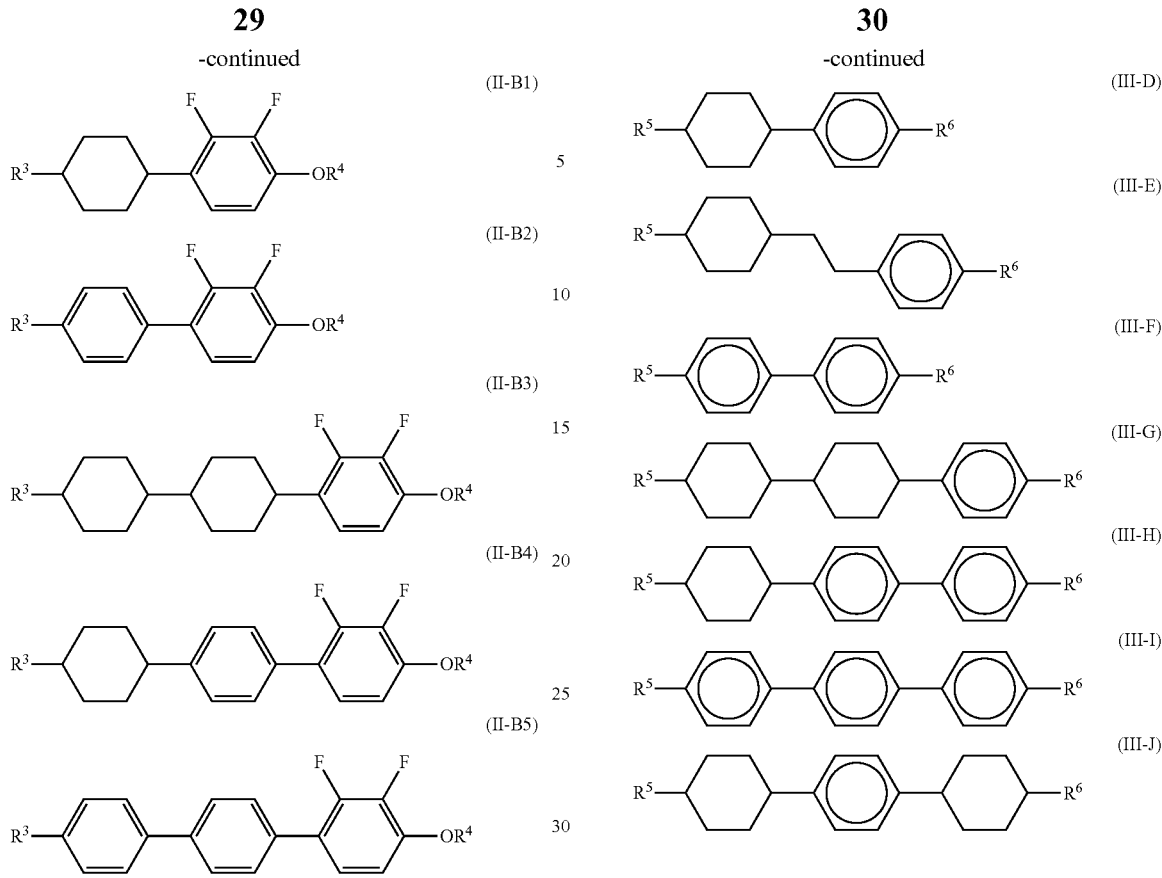

In the formulae, $R^3$ and $R^4$ each independently represent an alkyl group having 1 to 5 carbon atoms or an alkenyl group having 2 to 5 carbon atoms. one hydrogen atom or two or more hydrogen atoms existing in $R^3$ and $R^4$ each independently may be substituted with a fluorine atom.

The polymerizable compound-containing liquid crystal composition of the present invention includes one or two or more kinds of compounds selected from the group consisting of compounds represented by general formulae (III-A) to (III-J), as a compound having a dielectric anisotropy (Δε) of about 0, preferably one to ten kinds of compounds, and more preferably one to five kinds of compounds. The content thereof is 10 mass % to 90 mass %, more preferably 20 mass % to 70 mass %, and particularly preferably 30 mass % to 60 mass %.

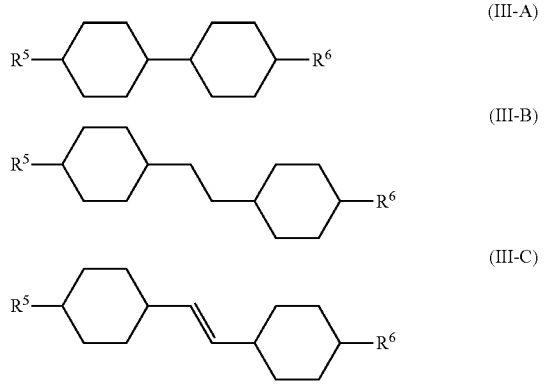

In the formulae, $R^5$ represents an alkyl group having 1 to 5 carbon atoms or an alkenyl group having 2 to 5 carbon atoms, and $R^6$ represents an alkyl group having 1 to 5 carbon atoms, an alkoxy group having 1 to 5 carbon atoms, an alkenyl group having 2 to 5 carbon atoms, or an alkenyloxy group having 2 to 5 carbon atoms.

As the compound having a dielectric anisotropy (Δε) of about 0, a compound represented by any one selected from general formulae (III-A), (III-D), (III-F), (III-G), and (III-H) is more preferable, and a compound represented by general formula (III-A) is particularly preferable. In the compound represented by general formula (III-A), it is preferable that $R^5$ is an alkenyl group having 2 to 5 carbon atoms, and $R^e$ is an alkyl group having 1 to 5 carbon atoms or an alkenyl group having 2 to 5 carbon atoms. The polymerizable compound-containing liquid crystal composition of the present invention preferably contains the compounds of general formula (M) and general formula (Na) at the same time, preferably contains the compounds of formula (XX-1) and general formula (Na) at the same time, preferably contains the compounds of formula (XX-2) and general formula (Na) at the same time, preferably contains the compounds of formula (XX-3) and general formula (Na) at the same time, preferably contains the compounds of formula (XX-4) and general formula (Na) at the same time, preferably contains the compounds of general formula (M) and general formula (Nb) at the same time, preferably contains the compounds of formula (XX-1) and general formula (Nb) at the same time, preferably contains the compounds of formula (XX-2) and general formula (Nb) at the same time, preferably contains the compounds of formula (XX-3) and general formula (Nb) at the same time, and preferably contains the compounds of formula (XX-4) and general formula (Nb) at the same time.

The polymerizable compound-containing liquid crystal composition of the present invention preferably contains the compounds of general formula (M), general formula (Na), and general formula (II-A1) at the same time, preferably contains the compounds of general formula (M), general formula (Na), and general formula (II-A3) at the same time, preferably contains the compounds of general formula (M), general formula (Na), and general formula (II-B1) at the same time, preferably contains the compounds of general formula (M), general formula (Na), and general formula (II-B2) at the same time, preferably contains the compounds of general formula (M), general formula (Na), and general formula (II-B3) at the same time, and preferably contains the compounds of general formula (M), general formula (Na), and general formula (II-B4) at the same time.

The polymerizable compound-containing liquid crystal composition of the present invention preferably contains the compounds of general formula (M), general formula (Na), general formula (II-A1), and general formula (III-A) at the same time, preferably contains the compounds of general formula (M), general formula (Na), general formula (II-A3), and general formula (III-A) at the same time, preferably contains the compounds of general formula (M), general formula (Na), general formula (II-B1), and general formula (III-A) at the same time, preferably contains the compounds of general formula (M), general formula (Na), general formula (II-B2), and general formula (III-A) at the same time, preferably contains the compounds of general formula (M), general formula (Na), general formula (II-B3), and general formula (III-A) at the same time, and preferably contains the compounds of general formula (M), general formula (Na), general formula (II-B4), and formula (III-A) at the same time. Particularly preferably, the polymerizable compound-containing liquid crystal composition of the present invention contains the compounds of general formula (M), general formula (Na), general formula (II-A1), general formula (II-A3), and general formula (III-A) at the same time.

The polymerizable compound-containing liquid crystal composition of the present invention preferably contains the compounds of general formula (M), general formula (Nb), and general formula (II-A1) at the same time, preferably contains the compounds of general formula (M), general formula (Nb), and general formula (II-A3) at the same time, preferably contains the compounds of general formula (M), general formula (Nb), and general formula (II-B1) at the same time, preferably contains the compounds of general formula (M), general formula (Nb), and general formula (II-B2) at the same time, preferably contains the compounds of general formula (M), general formula (Nb), and general formula (II-B3) at the same time, and preferably contains the compounds of general formula (M), general formula (Nb), and general formula (II-B4) at the same time.

The polymerizable compound-containing liquid crystal composition of the present invention preferably contains the compounds of general formula (M), general formula (Nb), general formula (II-A1), and general formula (III-A) at the same time, preferably contains the compounds of general formula (M), general formula (Nb), general formula (II-A3), and general formula (III-A) at the same time, preferably contains the compounds of general formula (M), general formula (Nb), general formula (II-B1), and general formula (III-A) at the same time, preferably contains the compounds of general formula (M), general formula (Nb), general formula (II-B2), and general formula (III-A) at the same time, preferably contains the compounds of general formula (M), general formula (Nb), general formula (II-B3), and general formula (III-A) at the same time, and preferably contains the compounds of general formula (M), general formula (Nb), general formula (II-B4), and general formula (III-A) at the same time. Particularly preferably, the polymerizable compound-containing liquid crystal composition of the present invention contains the compounds of general formula (M), general formula (Nb), general formula (II-A1), general formula (II-A3), and general formula (III-A) at the same time.

In the liquid crystal compound contained in the polymerizable compound-containing liquid crystal composition of the present invention, in order to suppress a display defect such as image persistence or display unevenness, or in order to completely prevent the occurrence of the display defect, it is preferable that a compound having an alkenyl group is not contained. Further, it is preferable that the side chain of all the liquid crystal compounds is an alkyl group or an alkoxy group. Moreover, the cyclohexane ring or benzene ring in the liquid-crystal compound may be substituted with a fluorine atom, but it is not preferable that the cyclohexane ring or the benzene ring is substituted with a chlorine atom.

In the liquid crystal display device that uses the liquid crystal composition containing the compounds of general formulae (M), (Na), (II), and (II-A), high-speed response is provided, and a display defect such as image persistence or display unevenness is extremely suppressed or does not occur at all. Here, the liquid crystal composition may contain a compound represented by general formula (Nb) instead of a compound represented by general formula (Na), and may also contain a compound represented by general formula (Nc) instead of a compound represented by general formula (Na), but it is most preferable that the liquid crystal composition contain a compound represented by general formula (Na).

The dielectric anisotropy ($\Delta\varepsilon$) of the polymerizable compound-containing liquid crystal composition of the present invention at 25° C. is −2.0 to −8.0, preferably −2.0 to −6.0, more preferably −2.0 to −5.0, and particularly preferably −2.5 to −4.0.

The refractive index anisotropy ($\Delta n$) of the liquid crystal composition of the present invention at 20° C. is 0.08 to 0.14, more preferably 0.09 to 0.13, and particularly preferably 0.09 to 0.12. More specifically, it is preferable that the refractive index anisotropy thereof is 0.10 to 0.13 when it corresponds to a thin cell gap, and it is preferable that the refractive index anisotropy thereof is 0.08 to 0.10 when it corresponds to a thick cell gap.

The viscosity ($\eta$) of the liquid crystal composition of the present invention at 20° C. is 10 mPa·s to 30 mPa·s, more preferably 10 mPa·s to 25 mPa·s, and particularly preferably 10 mPa·s to 22 mPa·s.

The rotational viscosity ($\gamma_1$) of the liquid crystal composition of the present invention at 20° C. is 60 mPa·s to 130 mPa·s, more preferably 60 mPa·s to 110 mPa·s, and particularly preferably 60 mPa·s to 100 mPa·s.

The nematic phase-isotropic liquid phase transition temperature ($T_{ni}$) of the liquid crystal composition of the present invention is 60° C. to 120° C., more preferably 70° C. to 100° C., and particularly preferably 70° C. to 85° C.

The polymerization of the polymerizable compound-containing liquid crystal composition of the present invention proceeds even if a polymerization initiator does not exist, but this liquid crystal composition may contain a polymerization initiator in order to accelerate the polymerization. Examples of the polymerization initiator include benzoin ethers, benzophenones, acetophenones, benzyl ketals, and acylphosphine oxides.

The polymerizable compound-containing liquid crystal composition of the present invention may further include a compound represented by general formula (Q).

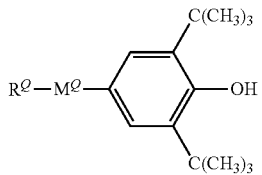

In the formula, $R^Q$ represents a linear alkyl group having 1 to 22 carbon atoms or a branched alkyl group having 1 to 22 carbon atoms, and one $CH_2$ group or two or more non-adjacent $CH_2$ groups in the group may be substituted with —O—, —CH=CH—, —CO—, —OCO—, —COO—, —C≡C—, —CF$_2$O—, or —OCF$_2$—.

$M^Q$ represents a trans-1,4-cyclohexylene group, a 1,4-phenylene group, or a single bond.

Specifically, it is preferable that examples of the compound represented by general formula (Q) include compounds represented by the following general formulae (Q-a) to (Q-d).

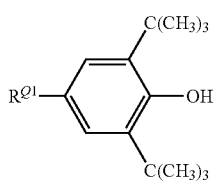

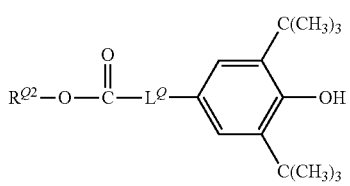

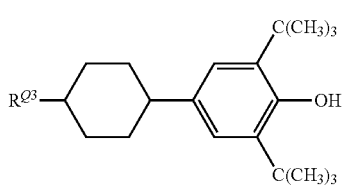

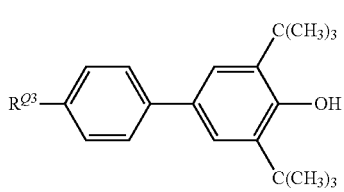

In the formulae, $R^{Q1}$ is preferably a linear alkyl group or branched alkyl group having 1 to 10 carbon atoms.

$R^{Q2}$ is preferably a linear alkyl group or branched alkyl group having 1 to 20 carbon atoms.

$R^{Q3}$ is preferably a linear alkyl group or branched alkyl group having 1 to 8 carbon atoms, or a linear alkoxy group or branched alkoxy group having 1 to 8 carbon atoms.

$L^Q$ is preferably a linear alkylene group or branched alkylene group having 1 to 8 carbon atoms.

Among the compounds represented by general formulae (Q-a) to (Q-d), the compounds represented by general formulae (Q-c) and (Q-d) are more preferable.

The polymerizable compound-containing liquid crystal composition of the present invention includes one or two or more kinds of compounds represented by general formula (Q), preferably one to five kinds of compounds, more preferably one to three kinds of compounds, and particularly preferably one kind of compound. The content thereof is preferably 0.001 mass % to 1 mass %, more preferably 0.001 mass % to 0.1 mass %, and particularly preferably 0.001 mass % to 0.05 mass %.

Further, in order to improve storage stability, a stabilizer may be added. Examples of the stabilizer which can be used include hydroquinones, hydroquinone monoalkyl ethers, tertiary butyl catechols, pyrogallols, thiophenols, nitro compounds, β-naphthylamines, β-naphthols, and nitroso compounds.

The polymerizable compound-containing liquid crystal composition of the present invention may include general nematic liquid crystal, smectic liquid crystal, cholesteric liquid crystal, an antioxidant, an ultraviolet absorber, or a polymerizable monomer in addition to the compounds described above.

The polymerizable compound-containing liquid crystal composition of the present invention is useful for a liquid crystal display device, and particularly useful for a liquid crystal display device for active matrix driving, and can be used for a liquid crystal display device for a PSA mode, a PSVA mode, a VA mode, an IPS mode, or an ECB mode.

The liquid crystal alignment ability is imparted to the polymerizable compound-containing liquid crystal composition of the present invention by polymerizing the polymerizable compound contained in the liquid crystal composition by irradiation with ultraviolet rays, and the liquid crystal composition is used for a liquid crystal display device which controls the quantity of transmitted light using the birefringence of the liquid crystal composition. The liquid crystal composition is useful for, as liquid crystal display devices, an AM-LCD (active-matrix liquid crystal display device), a TN (nematic liquid crystal display device), a STN-LCD (super-twisted nematic liquid crystal display device), an OCB-LCD, and an IPS-LCD (in-plane switching liquid crystal display device). Among these, the liquid crystal composition is particularly useful for an AM-LCD, and can be used for a transmission type or reflection type liquid crystal display device.

Two sheets of substrates of liquid crystal cells being used for the liquid crystal display device may use glass or transparent materials having flexibility such as plastic, or may use opaque materials such as silicon for one of the substrates. A transparent substrate having a transparent electrode layer can be obtained by sputtering indium tin oxide (ITO) on the transparent substrate such as a glass plate.

A color filter can be prepared by, for example, a pigment dispersion method, a printing method, an electrodeposition method, or a dyeing method. The method of preparing a color filter using a pigment dispersion method will be described as an example. A curable coloring composition for a color filter is coated on the transparent substrate, a patterning treatment is applied thereto, and the composition is allowed to be cured by heating or irradiation with light. A pixel portion for a color filter can be prepared by performing this process with each of three colors, which are red, green, and blue. In addition, a pixel electrode on which a TFT, a thin film diode, or an active element such as a metal-insulator-metal specific resistance element is provided may be provided on the substrate.

The substrates are allowed to face each other such that the transparent electrode layer is located inside. At this time, the space between substrates may be adjusted via a spacer. The thickness of a light adjusting layer to be obtained is preferably adjusted such that the thickness thereof is in the range of 1 µm to 100 µm. The thickness thereof is more preferably in the range of 1.5 µm to 10 µm, and it is preferable to adjust the product of refractive index anisotropy Δn and cell thickness d of the liquid crystal such that the contrast thereof becomes the maximum when a polarization plate is used. Further, when two polarization plates are present, a view angle or contrast of the polarization plates can be adjusted to be excellent by adjusting the polarization axis of each of the polarization plates. In addition, a phase difference film can be used to widen the view angle. Examples of the spacer may include glass particles, plastic particles, alumina particles, and photoresist materials. Subsequently, screen printing of a sealant of an epoxy-based thermosetting composition or the like is performed on the substrates in a state of providing a liquid crystal injection port, and then the substrates are bonded to each other and heated to heat-cure the sealant.

As a method of interposing a polymerizable compound-containing liquid crystal composition between two substrates, a vacuum injection method or an ODF method can be used in the usual manner.

As a method of polymerizing a polymerizable compound, a method of polymerizing a polymerizable compound by irradiation with active energy rays such as ultraviolet rays or electron rays which are used singly, in combination or in order is preferable because appropriate polymerization rate is desirable in order to obtain good liquid crystal alignment performance. In a case of using ultraviolet rays, a polarization light source or a non-polarization light source may be used. Further, in a case where polymerization is performed in a state in which a polymerizable compound-containing liquid crystal composition is interposed between two sheets of substrates, appropriate transparency with respect to the active energy rays is necessarily applied to at least the substrate on the irradiation surface side. Alternatively, polymerization may be performed by polymerizing only a specific portion using a mask at the time of irradiation with light, changing the conditions such as an electric field, a magnetic field, or a temperature to change the state of alignment of the non-polymerized portion, and further performing irradiation with active energy rays. Particularly, at the time of exposure to ultraviolet rays, it is preferable to perform exposure to ultraviolet rays by applying the alternating electric field to a polymerizable compound-containing liquid crystal composition. The frequency of the alternating electric field to be applied is preferably in the range of 10 Hz to 10 kHz and more preferably in the range of 60 Hz to 10 kHz, and the voltage is selected depending on a desired pretilt angle of the liquid crystal display device. That is, it is possible to control the pretilt angle of the liquid crystal display device by the voltage to be applied. In the liquid crystal display device with the MVA mode, the pretilt angle is preferably controlled to be in the range of 80° to 89.9° from a viewpoint of the alignment stability and the contrast.

The temperature at the time of irradiation is preferably in the temperature range in which the state of the liquid crystal in the liquid crystal composition of the present invention is maintained. It is preferable to perform polymerization at a temperature close to room temperature, that is, typically a temperature of 15° C. to 35° C. As a lamp generating ultraviolet rays, a metal halide lamp, a high-pressure mercury lamp, or an ultrahigh-pressure mercury lamp can be used. As a wavelength of ultraviolet rays used for irradiated, it is preferable to perform irradiation with ultraviolet rays in the wavelength region which is not the absorption wavelength region of the liquid crystal composition, and it is preferable that ultraviolet rays be cut to be used if necessary. The intensity of ultraviolet rays used for irradiation is preferably in the range of 0.1 mW/cm$^2$ to 100 W/cm$^2$ and more preferably in the range of 2 mW/cm$^2$ to 50 W/cm$^2$. The amount of energy of ultraviolet rays used for irradiation can be appropriately adjusted, but the amount thereof is preferably in the range of 10 mJ/cm$^2$ to 500 J/cm$^2$ and more preferably in the range of 100 mJ/cm$^2$ to 200 J/cm$^2$. The intensity thereof may be changed when irradiating with ultraviolet rays. The irradiation time of ultraviolet rays is appropriately selected depending on the intensity of ultraviolet rays used for irradiation, but the time thereof is preferably in the range of 10 seconds to 3600 seconds, and more preferably in the range of 10 seconds to 600 seconds.

EXAMPLES

Hereinafter, the present invention will be described in more detail with reference to the following examples, but the present invention is not limited thereto. Further, "%" in the compositions of the following examples and comparative examples means "mass %."

The following abbreviations are used for the description of the compounds in the examples.
(Side Chain)
-n —$C_nH_{2n+1}$ linear alkyl group having n carbon atoms
n- $CH_nH_{2n+1}$— linear alkyl group having n carbon atoms
—On —$OC_nH_{2n+1}$ linear alkoxy group having n carbon atoms
nO— $C_nH_{2n+1}O$— linear alkoxy group having n carbon atoms
—V —CH=CH$_2$
V— CH$_2$=CH—
—V1 —CH=CH—CH$_3$
1V— CH$_3$—CH=CH—
-2V —CH$_2$—CH$_2$—CH=CH$_3$
V2- CH=CH—CH$_2$—CH$_2$—
-2V1 -CH$_2$—CH$_2$—CH=CH—CH$_3$
1V2- CH$_3$—CH=CH—CH$_2$—CH$_2$
(Linking Group)
—CF2O— —CF$_2$—O—
—OCF2- —O—CF$_2$—
-1O— —CH$_2$—O—
—O1- —O—CH$_2$—
—COO— —COO—
(Ring Structure)

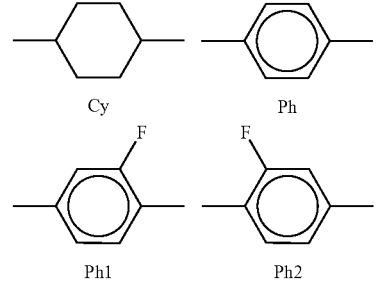

Cy        Ph
Ph1       Ph2

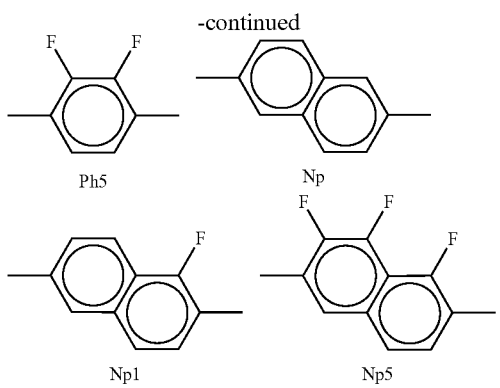

The measured physical properties of the liquid crystal compositions in the examples are as follows.

$T_{ni}$: nematic phase-isotropic liquid phase transition temperature (° C.)

Δn: refractive index anisotropy at 20° C.

η: viscosity at 20° C. (mPa·s)

γ1: rotational viscosity at 20° C. (mPa·s)

Δε: dielectric anisotropy at 25° C.

Residual amount of polymerizable compound @10[J]: residual amount [%] of polymerizable compound after irradiation with 10 J of UV Residual amount of polymerizable compound @20[J]: residual amount [%] of polymerizable compound after irradiation with 20 J of UV Residual amount of polymerizable compound @50[J]: residual amount [%] of polymerizable compound after irradiation with 50 J of UV Residual amount of polymerizable compound @60[J]: residual amount [I] of polymerizable compound after irradiation with 60 J of UV Pretilt angle: tilt angle [°] after irradiation with 10 J of UV Comparative Example 1, Examples 1 and 2

Polymerizable compound-containing liquid crystal compositions LC-A (Comparative Example 1), LC-1 (Example 1) and LC-2 (Example 2) were prepared, and physical property values thereof were measured. Configurations and results of physical property values of the polymerizable compound-containing liquid crystal compositions are listed in Table 1.

TABLE 1

|  | LC100 | Comp. Ex. 1 LC-A | Ex. 1 LC-1 | Ex. 2 LC-2 |
| --- | --- | --- | --- | --- |
| Polymerizable compound formula (XX-4) | — | 0.4 | 0.4 | 0.4 |
| 3-Np—Ph5—Ph-2 general formula (N-049) | — | — | 2 | 4 |
| LC100 Liquid crystal composition | — | 99.6 | 97.6 | 95.6 |
| 2-Cy-Cy-V1 general formula (III-A) | 4 | — | — | — |
| 3-Cy-Cy-V1 general formula (III-A) | 4 | — | — | — |
| 3-Cy-Cy-V general formula (III-A) | 4 | — | — | — |
| 3-Cy-Cy-2 general formula (III-A) | 14 | — | — | — |
| 3-Cy-Cy-4 general formula (III-A) | 4 | — | — | — |

TABLE 1-continued

|  | LC100 | Comp. Ex. 1 LC-A | Ex. 1 LC-1 | Ex. 2 LC-2 |
| --- | --- | --- | --- | --- |
| 3-Ph—Ph-1 general formula (III-F) | 10 | — | — | — |
| 5-Ph—Ph-1 general formula (III-F) | 6 | — | — | — |
| 3-Cy-Cy-Ph-1 general formula (III-G) | 1 | — | — | — |
| 3-Cy-Ph—Ph-2 general formula (III-H) | 1 | — | — | — |
| 1V-Cy-1O—Ph5—O2 general formula (II-A1) | 2 | — | — | — |
| 2-Cy-Cy-1O—Ph5—O2 general formula (II-A3) | 3 | — | — | — |
| 3-Cy-Cy-1O—Ph5—O2 general formula (II-A3) | 3 | — | — | — |
| V-Cy-Cy-1O—Ph5—O2 general formula (II-A3) | 8 | — | — | — |
| 1V-Cy-1O—Ph5—O2 general formula (II-A3) | 10 | — | — | — |
| 3-Cy-Ph5—O2 general formula (II-B1) | 3 | — | — | — |
| 3-Ph—Ph5—O2 general formula (II-B2) | 3 | — | — | — |
| 3-Cy-Cy-Ph5—O2 general formula (II-B3) | 3 | — | — | — |
| 3-Cy-Ph—Ph5—O2 general formula (II-B4) | 4 | — | — | — |
| 3-Cy-Ph—Ph5—O3 general formula (II-B4) | 7 | — | — | — |
| 3-Cy-Ph—Ph5—O4 general formula (II-B4) | 6 | — | — | — |
| Total | 100 | 100 | 100 | 100 |
| $T_{ni}$ [° C.] | 77.5 | 77.3 | 79.1 | 80.7 |
| Δn | 0.108 | 0.108 | 0.111 | 0.115 |
| η [mPa · s] | 17.1 | 17.1 | 17.7 | 18.2 |
| Δε | −3.1 | −3.1 | −3.1 | −3.1 |
| Residual amount of polymerizable compound @ 10 [J] | — | 65 | 50 | 38 |
| Residual amount of polymerizable compound @ 50 [J] | — | 23 | 5 | 2 |
| Pretilt angle [°] | — | 85 | 85 | 85 |

Each of LC-1 and LC-2 was injected into a cell with ITO at the cell gap of 3.5 μm, in which a polyamide alignment film inducing homeotropic alignment was coated, using a vacuum injection method. The cell was irradiated with ultraviolet rays using a high-pressure mercury lamp via a filter cutting ultraviolet ray having a wavelength of 320 nm or less while applying a square wave at 1.8 V with a frequency of 1 kHz. The UV irradiation was adjusted such that the irradiation intensity on the surface of the cell became 100 mW/cm², thereby obtaining a vertical aligning liquid crystal display device in which the polymerizable compound in the polymerizable compound-containing liquid crystal composition is polymerized. It was confirmed that this liquid crystal display device (PSVA mode) exhibits a high contrast and a sufficiently fast response.

When irradiation was performed with 10[J] of UV, the residual amount of the polymerizable compound in LC-A was 65[%], the residual amount of the polymerizable compound in LC-1 was 50[%], and the residual amount of the polymerizable compound in LC-2 was 38[%].

When irradiation was performed with 50[J] of UV, the residual amount of the polymerizable compound in LC-A was 23[%], the residual amount of the polymerizable compound in LC-1 was 5[%], and the residual amount of the polymerizable compound in LC-2 was 2[%]

It was confirmed that each of the residual amounts of the polymerizable compound in LC-1 and LC-2 (polymerizable compound-containing liquid crystal compositions of the present invention) is sufficiently small compared to the residual amount of the polymerizable compound in LC-A (polymerizable compound-containing liquid crystal composition of Comparative Example 1), and that, in the case of LC-1 and LC-2, the polymerization of the polymerizable compound sufficiently proceed by lower UV irradiation intensity compared to in the case of LC-A.

Further, it was confirmed that all of LC-1 and LC-2 (polymerizable compound-containing liquid crystal compositions of the present invention), and LC-A (polymerizable compound-containing liquid crystal composition of Comparative Example 1) have a pretilt angle of 85[°], and their alignment controls are sufficiently possible. Here, the pretilt angle was measured at 25° C. using TBA 105 of AUTRONIC-MELCHERS Corporation.

Comparative Example 2, Examples 3 and 4

Polymerizable compound-containing liquid crystal compositions LC-B (Comparative Example 2), LC-3 (Example 3), LC-4 (Example 4), and LC-5 (Example 5) were prepared, and physical property values thereof were measured.

Configurations and results of physical property values of the polymerizable compound-containing liquid crystal compositions are listed in Table 2.

TABLE 2

|  | LC200 | Comp. Ex. 2 LC-B | Ex. 3 LC-3 | Ex. 4 LC-4 | Ex. 5 LC-5 |
| --- | --- | --- | --- | --- | --- |
| Polymerizable compound formula (XX-2) | — | 0.1 | — | 0.4 | 0.1 |
| Polymerizable compound formula (XX-4) | — | 0.2 | 0.3 | — | — |
| Polymerizable compound formula (M-302) | — | — | — | — | 0.3 |
| 3-Np—Ph5—Ph-2 general formula (N-049) | — | — | 2 | 4 | — |
| 2-Cy-Ph—1O—Np5—O2 general formula (N-074) | — | — | — | — | 4 |
| LC200 Liquid crystal composition | — | 99.7 | 97.7 | 95.6 | 95.6 |
| 3-Cy-Cy-2 general formula (III-A) | 18 | — | — | — | — |
| 3-Cy-Cy-4 general formula (III-A) | 8 | — | — | — | — |
| 3-Ph—Ph-1 general formula (III-F) | 10 | — | — | — | — |
| 5-Ph—Ph-1 general formula (III-F) | 8 | — | — | — | — |
| 3-Cy-Cy-Ph-1 general formula (III-G) | 4 | — | — | — | — |
| 3-Cy-1O—Ph5—O2 general formula (II-A1) | 8 | — | — | — | — |
| 2-Cy-Cy-1O—Ph5—O2 general formula (II-A3) | 11 | — | — | — | — |
| 3-Cy-Cy-1O—Ph5—O2 general formula (II-A3) | 11 | — | — | — | — |
| 3-Cy-Ph—Ph5—O2 general formula (II-B4) | 6 | — | — | — | — |
| 3-Cy-Ph—Ph5—O3 general formula (II-B4) | 7 | — | — | — | — |
| 3-Cy-Ph—Ph5—O4 general formula (II-B4) | 9 | — | — | — | — |
| Total | 100 | 100 | 100 | 100 | 100 |
| Tni[° C.] | 75.1 | 74.9 | 76.7 | 78.5 | 79.1 |
| Δn | 0.108 | 0.108 | 0.112 | 0.116 | 0.115 |
| η[mPa·s] | 18.5 | 18.5 | 19.1 | 19.8 | 19.8 |
| γ1[mPa·s] | 127 | 127 | 128 | 133 | 135 |
| Δε | −3.1 | −3.1 | −3.1 | −3.1 | −3.2 |
| Residual amount of polymerizable compound @ 20 [J] | — | 55 | 47 | 34 | 33 |
| Residual amount of polymerizable compound @ 60 [J] | — | 18 | 9 | 3 | 2 |
| Pretilt angle [°] | — | 86 | 86 | 86 | 85 |

Each of the polymerizable compound-containing liquid crystal compositions shown in Table 2 was injected into a cell with ITO at the cell gap of 3.5 μm, in which a polyimide alignment film inducing homeotropic alignment was coated, using a vacuum injection method. The cell was irradiated with ultraviolet rays using a high-pressure mercury lamp via a filter cutting ultraviolet ray having a wavelength of 320 nm or less while applying a square wave at 1.8 V with a frequency of 1 kHz. The UV irradiation was adjusted such that the irradiation intensity on the surface of the cell became 100 mW/cm$^2$, thereby obtaining a vertical aligning liquid crystal display device in which the polymerizable compound in the polymerizable compound-containing liquid crystal composition is polymerized. It was confirmed that this liquid crystal display device (PSVA mode) exhibits a high contrast and a sufficiently fast response.

When irradiation was performed with 20[J] of UV, the residual amount of the polymerizable compound in LC-B was 55[%], the residual amount of the polymerizable compound in LC-3 was 47[%], the residual amount of the polymerizable compound in LC-4 was 38[%], and the residual amount of the polymerizable compound in LC-5 was 39[%].

When irradiation was performed with 60[J] of UV, the residual amount of the polymerizable compound in LC-B was 18 [%], the residual amount of the polymerizable compound in LC-3 was 9[%], the residual amount of the polymerizable compound in LC-4 was 4 [%], and the residual amount of the polymerizable compound in LC-5 was 5[%].

It was confirmed that each of the residual amounts of the polymerizable compound in LC-3, LC-4, and LC-5 (polymerizable compound-containing liquid crystal compositions of the present invention) is sufficiently small compared to the residual amount of the polymerizable compound in LC-B (polymerizable compound-containing liquid crystal composition of Comparative Example 2), and that, in the case of LC-3, LC-4 and LC-5, the polymerization of the polymerizable compound sufficiently proceeds by lower UV irradiation intensity compared to in the case of LC-B.

Further, it was confirmed that all of LC-3, LC-4, and LC-5 (polymerizable compound-containing liquid crystal compositions of the present invention), and LC-B (polymerizable compound-containing liquid crystal composition of Comparative Example 2) have a pretilt angle of 85 [°] to 86 [°], and their alignment controls are sufficiently possible. Here, the pretilt angle was measured at 25° C. using TBA 105 of AUTRONIC-MELCHERS Corporation.

Comparative Example 3, Examples 6 to 9

Polymerizable compound-containing liquid crystal compositions LC-C(Comparative Example 3), LC-6 (Example 6), LC-7 (Example 7), LC-8 (Example 8), and LC-9 (Example 9) were prepared, and physical property values thereof were measured. Configurations and results of physical property values of the polymerizable compound-containing liquid crystal compositions are listed in Table 3.

TABLE 3

|  | LC300 | Comp. Ex. 3 LC-C | Ex. 6 LC-6 | Ex. 7 LC-7 | Ex. 8 LC-8 | Ex. 9 LC-9 |
|---|---|---|---|---|---|---|
| Polymerizable compound formula (M-31) | — | 0.1 | — | — | 0.1 | 0.1 |
| Polymerizable compound formula (M-40) | — | 0.2 | — | — | 0.1 | 0.2 |
| Polymerizable compound formula (XX-2) | — | — | — | 0.4 | 0.1 | — |
| Polymerizable compound formula (XX-4) | — | — | 0.4 | — | 0.1 | — |
| Polymerizable compound formula (M-313) | — | — | — | — | — | 0.3 |
| 3-Np—Ph5—Ph-2 general formula (N-049) | — | — | 7 | 14 | 3 | — |
| 3-Np—Ph-2 general formula (Na) | — | — | — | — | 3 | — |
| 3-Np5—Ph—Ph—Ph-1 general formula (N-065) | — | — | — | — | — | 2 |
| 3-Np5—Ph—Ph—Ph-2 general formula (N-065) | — | — | — | — | — | 2 |
| 3-Np5—Ph—Ph—Ph-3 general formula (N-065) | — | — | — | — | — | 2 |
| LC300 Liquid crystal composition | — | 99.7 | 92.6 | 85.6 | 93.6 | 93.4 |
| 3-Cy-Cy-V general formula (III-A) | 10 | — | — | — | — | — |
| 3-Cy-Cy-2 general formula (III-A) | 8 | — | — | — | — | — |
| 3-Cy-Cy-4 general formula (III-A) | 8 | — | — | — | — | — |
| 3-Ph—Ph-1 general formula (III-F) | 10 | — | — | — | — | — |
| 5-Ph—Ph-1 general formula (III-F) | 8 | — | — | — | — | — |
| 3-Cy-Cy-Ph-1 general formula (III-G) | 4 | — | — | — | — | — |
| 3-Cy-1O—Ph5—O2 general formula (II-A1) | 8 | — | — | — | — | — |
| 2-Cy-Cy-1O—Ph5—O2 general formula (II-A3) | 11 | — | — | — | — | — |
| 3-Cy-Cy-1O—Ph5—O2 general formula (II-A3) | 11 | — | — | — | — | — |
| 3-Cy-Ph—Ph5—O2 general formula (II-B4) | 6 | — | — | — | — | — |
| 3-Cy-Ph—Ph5—O3 general formula (II-B4) | 7 | — | — | — | — | — |
| 3-Cy-Ph—Ph5—O4 general formula (II-B4) | 9 | — | — | — | — | — |
| Total | 100 | 100 | 100 | 100 | 100 | 100 |
| Residual amount of polymerizable compound @ 20 [J] | — | 58 | 23 | 10 | 30 | 28 |
| Residual amount of polymerizable compound @ 60 [J] | — | 20 | 0 | 0 | 2 | 2 |
| Pretilt angle [°] | — | 85 | 85 | 84 | 86 | 85 |

Each of the polymerizable compound-containing liquid crystal compositions shown in Table 3 was injected into a cell with ITO at the cell gap of 3.5 μm, in which a polyimide alignment film inducing homeotropic alignment was coated, using a vacuum injection method. The cell was irradiated with ultraviolet rays using a high-pressure mercury lamp via a filter cutting ultraviolet ray having a wavelength of 320 nm or less while applying a square wave at 1.8 V with a frequency of 1 kHz. The UV irradiation was adjusted such that the irradiation intensity on the surface of the cell became 100 mW/cm$^2$, thereby obtaining a vertical aligning liquid crystal display device in which the polymerizable compound in the polymerizable compound-containing liquid crystal composition is polymerized. It was confirmed that this liquid crystal display device (PSVA mode) exhibits a high contrast and a sufficiently fast response.

When irradiation was performed with 20[J] of UV, the residual amount of the polymerizable compound in LC-C was 58[%], the residual amount of the polymerizable compound in LC-6 was 23[%], the residual amount of the polymerizable compound in LC-7 was 10[%], the residual amount of the polymerizable compound in LC-8 was 30[%], and the residual amount of the polymerizable compound in LC-9 was 28[%].

When irradiation was performed with 60[J] of UV, the residual amount of the polymerizable compound in LC-C was 20[%], the residual amount of the polymerizable compound in LC-6 was 0[%], the residual amount of the polymerizable compound in LC-7 was 0[%], the residual amount of the polymerizable compound in LC-8 was 2[%], and the residual amount of the polymerizable compound in LC-9 was 2[%].

It was confirmed that each of the residual amounts of the polymerizable compound in LC-6, LC-7, LC-8, and LC-9 (polymerizable compound-containing liquid crystal compositions of the present invention) is sufficiently small compared to the residual amount of the polymerizable compound in LC-C (polymerizable compound-containing liquid crystal composition of Comparative Example 3), and that, in the case of LC-6, LC-7, LC-8, and LC-9, the polymerization of the polymerizable compound sufficiently proceeds by lower UV irradiation intensity compared to in the case of LC-C.

Further, it was confirmed that all of LC-6, LC-7, LC-8 and LC-9 (polymerizable compound-containing liquid crystal compositions of the present invention), and LC-C (polymerizable compound-containing liquid crystal composition of Comparative Example 3) have a pretilt angle of 84 [°] to 86 [°], and their alignment controls are sufficiently possible. Here, the pretilt angle was measured at 25° C. using TBA 105 of AUTRONIC-MELCHERS Corporation.

Comparative Example 4, Examples 10 and 11

Polymerizable compound-containing liquid crystal compositions LC-D (Comparative Example 4), LC-10 (Example 10), and LC-11 (Example 11) were prepared, and physical property values thereof were measured. Configurations and results of physical property values of the polymerizable compound-containing liquid crystal compositions are listed in Table 4.

TABLE 4

| | LC400 | Comp. Ex. 4 LC-D | Ex. 10 LC-10 | Ex. 11 LC-11 |
|---|---|---|---|---|
| Polymerizable compound formula (XX-2) | — | 0.15 | 0.15 | — |
| Polymerizable compound formula (XX-4) | — | 0.15 | 0.15 | — |
| Polymerizable compound formula (M302) | — | — | — | 0.4 |
| 3-Np—Ph5—Ph-2 general formula (N-049) | — | — | 3 | 3 |
| LC400 Liquid crystal composition | — | 99.7 | 96.7 | 96.6 |
| 3-Cy-Cy-V general formula (III-A) | 36 | — | — | — |
| 3-Cy-Cy-V1 general formula (III-A) | 7 | — | — | — |
| 3-Cy-Cy-Ph-1 general formula (III-G) | 2 | — | — | — |
| 3-Cy-Ph—Ph-2 general formula (III-H) | 2 | — | — | — |
| 3-Cy-Ph5—O2 general formula (II-B1) | 10 | — | — | — |
| 5-Cy-Ph5—O2 general formula (II-B1) | 3 | — | — | — |
| 3-Ph—Ph5—O2 general formula (II-B2) | 6 | — | — | — |
| 2-Cy-Cy-Ph5—O2 general formula (II-B3) | 8 | — | — | — |
| 3-Cy-Cy-Ph5—O2 general formula (II-B3) | 9 | — | — | — |
| 2-Cy-Ph—Ph5—O2 general formula (II-B4) | 8 | — | — | — |
| 3-Cy-Ph—Ph5—O2 general formula (II-B4) | 9 | — | — | — |
| Total | 100 | 100 | 100 | 100 |
| Residual amount of polymerizable compound @ 20 [J] | — | 64 | 27 | 23 |
| Residual amount of polymerizable compound @ 60 [J] | — | 31 | 2 | 1 |
| Pretilt angle [°] | — | 88 | 83 | 81 |

Each of the polymerizable compound-containing liquid crystal compositions shown in Table 4 was injected into a cell with ITO at the cell gap of 3.5 μm, in which a polyimide alignment film inducing homeotropic alignment was coated, using a vacuum injection method. The cell was irradiated with ultraviolet rays using a high-pressure mercury lamp via a filter cutting ultraviolet ray having a wavelength of 320 nm or less while applying a square wave at 1.8 V with a frequency of 1 kHz. The UV irradiation was adjusted such that the irradiation intensity on the surface of the cell became 100 mW/cm$^2$, thereby obtaining a vertical aligning liquid crystal display device in which the polymerizable compound in the polymerizable compound-containing liquid crystal composition is polymerized. It was confirmed that this liquid crystal display device (PSVA mode) exhibits a high contrast and a sufficiently fast response.

When irradiation was performed with 20[J] of UV, the residual amount of the polymerizable compound in LC-D was 64[%], the residual amount of the polymerizable compound in LC-10 was 27[%], and the residual amount of the polymerizable compound in LC-11 was 23[%].

When irradiation was performed with 60[J] of UV, the residual amount of the polymerizable compound in LC-D was 31[%], the residual amount of the polymerizable compound in LC-10 was 2[%], and the residual amount of the polymerizable compound in LC-11 was 1[%].

It was confirmed that each of the residual amounts of the polymerizable compound in LC-10 and LC-11 (polymerizable compound-containing liquid crystal compositions of the present invention) is sufficiently small compared to the residual amount of the polymerizable compound in LC-D (polymerizable compound-containing liquid crystal composition of Comparative Example 3), and that, in the case of LC-10 and LC-11, the polymerization of the polymerizable compound sufficiently proceeds by lower UV irradiation intensity compared to in the case of LC-D.

Further, it was confirmed that all of LC-10 and LC-11 (polymerizable compound-containing liquid crystal compositions of the present invention) have a pretilt angle of 83 [°] to 85 [°], and their alignment controls are sufficiently possible. Here, the pretilt angle was measured at 25° C. using TBA 105 of AUTRONIC-MELCHERS Corporation.

AS described above, since the polymerizable compound-containing liquid crystal composition of the present invention has a sufficiently low viscosity (η), the liquid crystal display device using the polymerizable compound-containing liquid crystal composition has a sufficiently fast response speed, and is capable of 3D display. Further, since the polymerizable compound does not remain or the residual amount thereof is sufficiently suppressed, display unevenness or image persistence does not occur or is extremely suppressed. Furthermore, since the polymerization reaction speed of the polymerizable compound is sufficiently fast, an energy cost for production can be reduced to improve the production efficiency, and uniform and stable orientation control can be obtained. Therefore, the polymerizable compound-containing liquid crystal composition of the present invention is very useful.

The invention claimed is:

1. A polymerizable compound-containing liquid crystal composition, comprising:
    at least one polymerizable compounds represented by general formula (M) as a first component;

(M)

(in the formula, $X^{201}$ and $X^{202}$ each independently represent a hydrogen atom, a methyl group, or a —$CF_3$ group; $Sp^{201}$ and $Sp^{202}$ each independently represent a single bond, an alkylene group having 1 to 8 carbon atoms, or —O—$(CH_2)_s$— (provided that, in the formula, s represents an integer of 2 to 7, and oxygen atom is bonded to a ring); ring $M^{201}$, ring $M^{202}$, and ring $M^{203}$ each independently represent a trans-1,4-cyclohexylene group (one —$CH_2$— or non-adjacent two or more —$CH_2$— in the group may be substituted with —O— or —S—), a 1,4-phenylene group (one —CH= or non-adjacent two or more —CH= in the group may be substituted with —N=), a 1,4-cyclohexenylene group, a 1,4-bicyclo [2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group; hydrogen atoms in the group each independently may be substituted with a fluorine atom, a —$CF_3$ group, an alkyl group having 1 to 10 carbon atoms, an alkoxy group having 1 to 10 carbon atoms, or any of formulae (R-1) to (R-15);

(R-1)

(R-2)

(R-3)

(R-4)

(R-5)

(R-6)

(R-7)

(R-8)

(R-9)

(R-10)

(R-11)

(R-12)

(R-13)

(R14)

(R-15)

$Z^{201}$ and $Z^{202}$ each independently represents —$OCH_2$—, —$CH_2O$—, —COO—, —OCO—, —$CF_2O$—, —$OCF_2$—, —$CH_2CH_2$—, —$CF_2CF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —$CY^1$=$CY^2$— (in the formulae, $Y^1$ and $Y^2$ each independently represent a fluorine atom or a hydrogen atom), —C≡C—, or a single bond; $n^{201}$ represents 0, 1, or 2; and when ring $M^{202}$ and $Z^{202}$ plurally exist, respectively, they may be different from each other or the same as each other, respectively); and at least one compounds selected from the group consisting of liquid crystal compounds represented by general formula (Na), general formula (Nb), or general formula (Nc), as a second component, (Na)

(Nb)

(Nc)

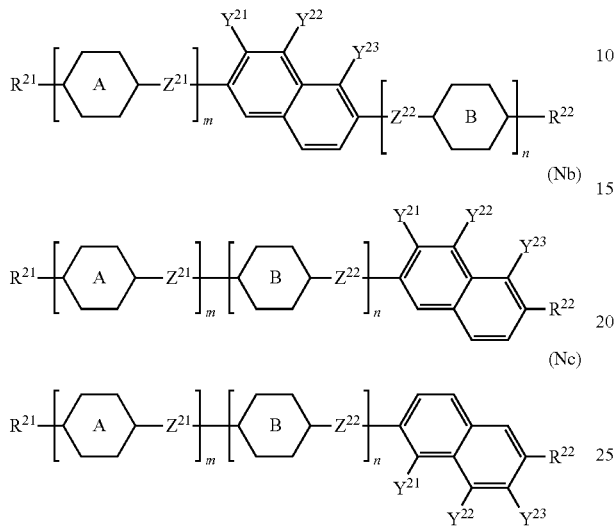

(in the formulae, $R^{21}$ and $R^{22}$ each independently represent an alkyl group having 1 to 10 carbon atoms, an alkoxy group having 1 to 10 carbon atoms, an alkenyl group having 2 to 10 carbon atoms, or an alkenyloxy group having 2 to 10 carbon atoms, and one or two or more hydrogen atoms existing in these groups may be substituted with fluorine atoms; $Y^{21}$ to $Y^{23}$ each independently represent a hydrogen atom, a methyl group, a —$CF_3$ group, a fluorine atom, or a chlorine atom; ring A and ring B each independently represent a trans-1,4-cyclohexylene group (one —$CH_2$— or two or more non-adjacent —$CH_2$— in the group may be substituted with —O— or —S—), a 1,4-phenylene group (one —CH═ or two or more non-adjacent —CH═ in the group may be substituted with —N═), a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group; $Z^{21}$ and $Z^{22}$ each independently represent —$OCH_2$—, —$CH_2O$—, —COO—, —OCO—, —$CF_2O$—, —$OCF_2$—, —$CH_2CH_2$—, —$CF_2CF_2$—, —C≡C— or a single bond; m represents 0, 1, or 2; when ring A and $Z^{21}$ plurally exist, respectively, they may be different from each other or the same as each other, respectively; n represents 0, 1, or 2; and when ring B and $Z^{22}$ plurally exist, respectively, they may be different from each other or the same as each other, respectively).

2. The polymerizable compound-containing liquid crystal composition according to claim 1, wherein the polymerizable compound represented by general formula (M) is selected from compounds represented by formulae (XX-1) to (XX-10),

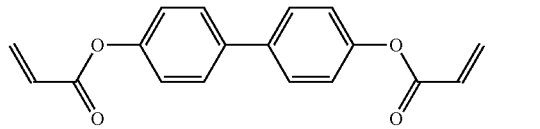
(XX-1)

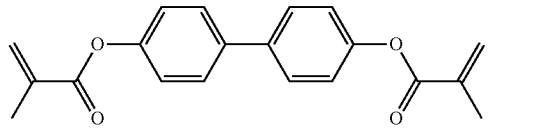
(XX-2)

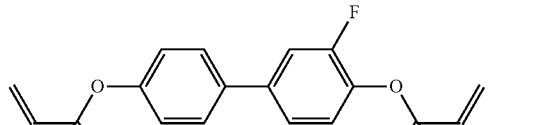
(XX-3)

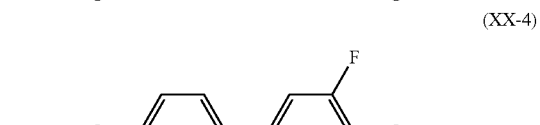
(XX-4)

(XX-5)

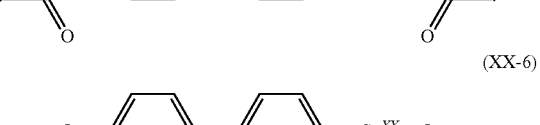
(XX-6)

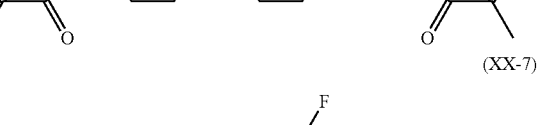
(XX-7)

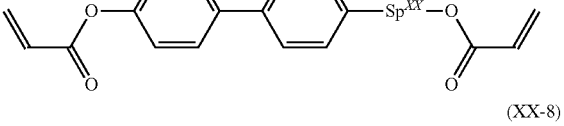
(XX-8)

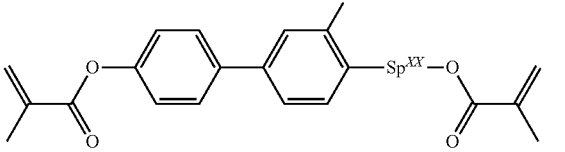
(XX-9)

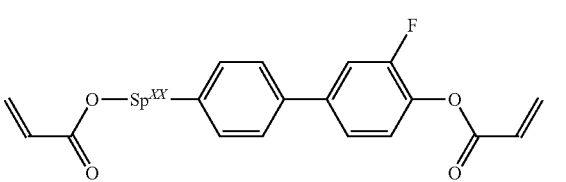

-continued

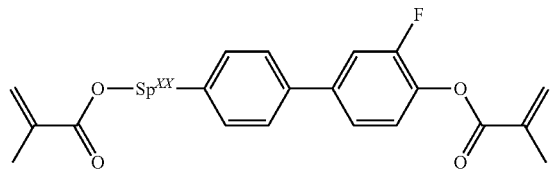
(XX-10)

(in the formulae, $Sp^{xx}$ represents an alkylene group having 1 to 8 carbon atoms or $-O-(CH_2)_s-$ (provided that, in the formula, s is an integer of 2 to 7, and an oxygen atom is bonded to a ring); and the hydrogen atom in the phenyl group may be substituted with $-F$, $-Cl$, $-CF_3$, $-CH_3$, or any one of formulae (R-1) to (R-15).

3. The polymerizable compound-containing liquid crystal composition according to claim 1, wherein the polymerizable compound represented by general formula (M) is selected from compounds represented by formulae (M31) to (M48), (M31)
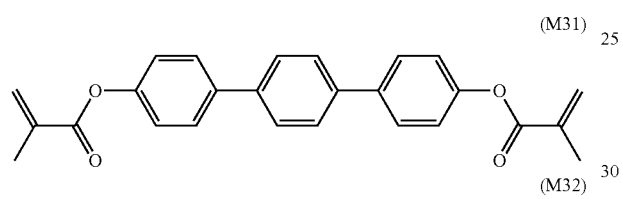

(M32)
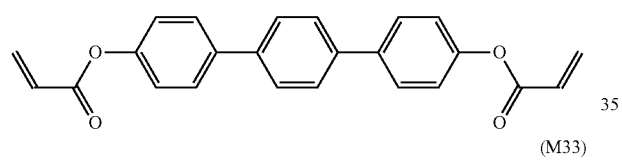

(M33)
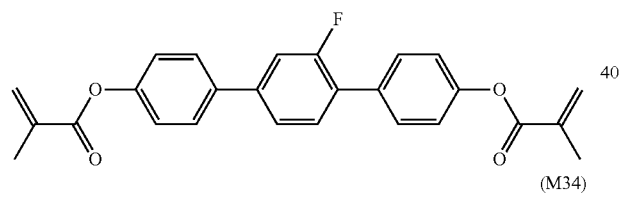

(M34)
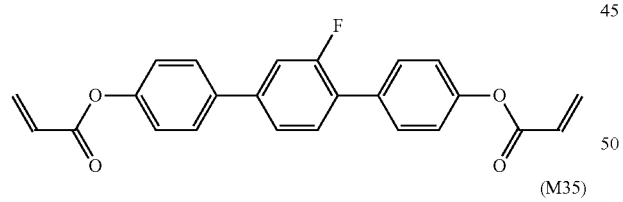

(M35)
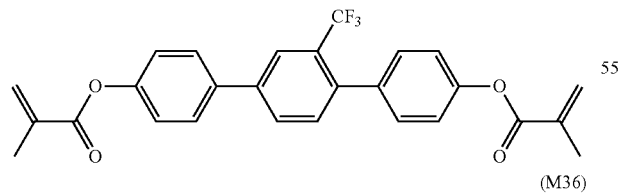

(M36)
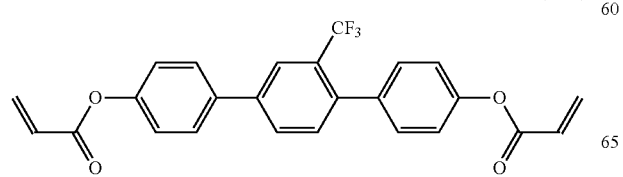

-continued (M37)
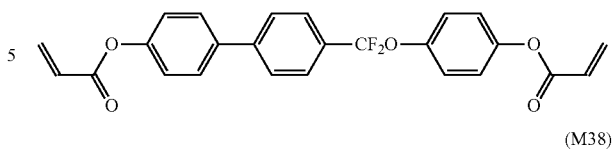

(M38)

(M39)
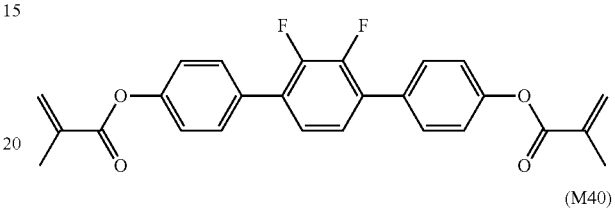

(M40)
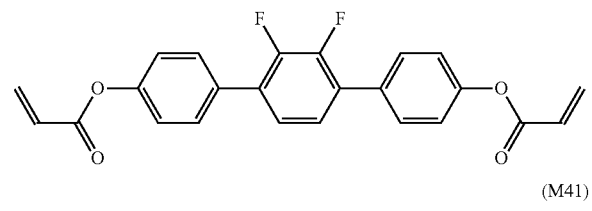

(M41)
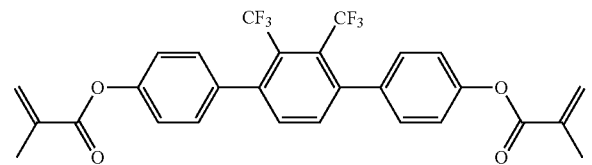

(M42)
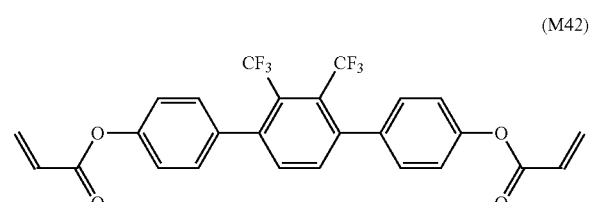

(M43)
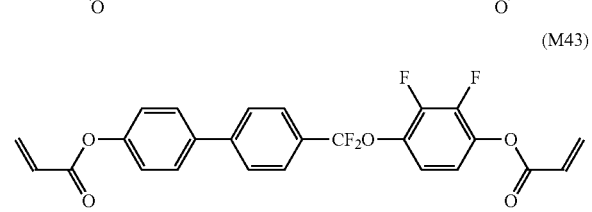

(M44)
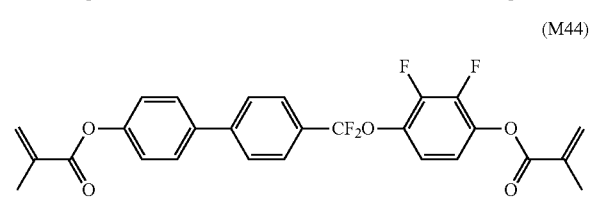

(M45)
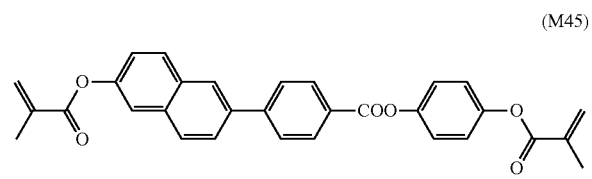

(M46)

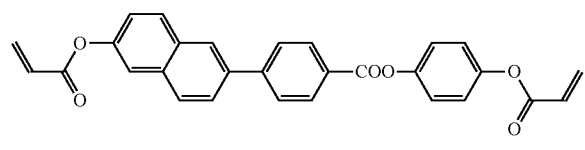

(M47)

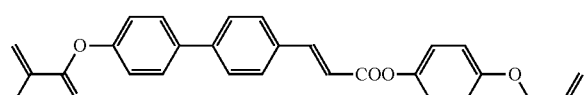

(M48)

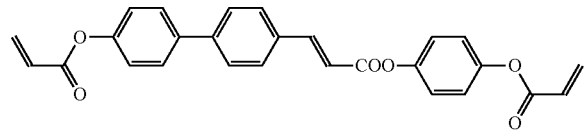

(in the formulae, each of the hydrogen atoms in the phenylene group and naphthalene group may be substituted with —F, —Cl, —CF$_3$, —CH$_3$, or any one of formulae (R-1) to (R-15).

4. The polymerizable compound-containing liquid crystal composition according to claim 1,
wherein the polymerizable compound represented by general formula (M) is selected from compounds represented by formulae (M301) to (M316), (M301)

(M302)

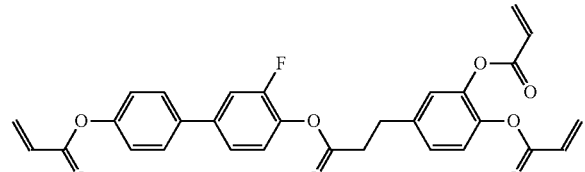

(M303)

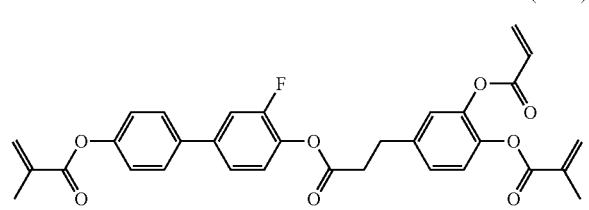

(M304)

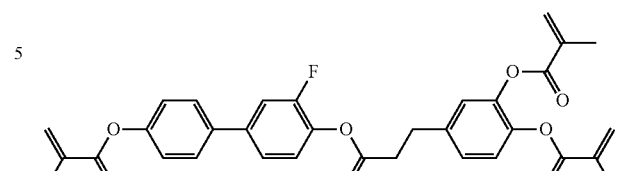

(M305)

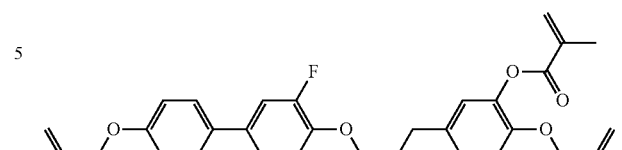

(M306)

(M307)

(M308)

(M309)

(M310)

-continued (M311)
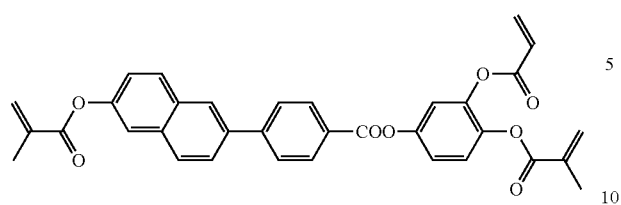

(M312)
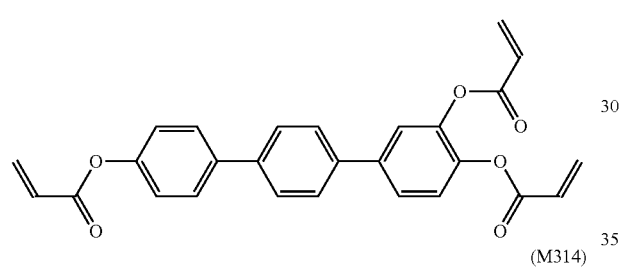

(M313)
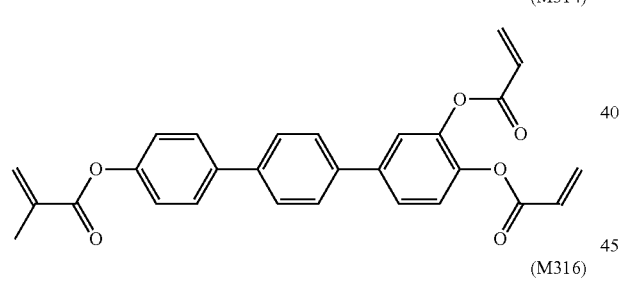

(M314)
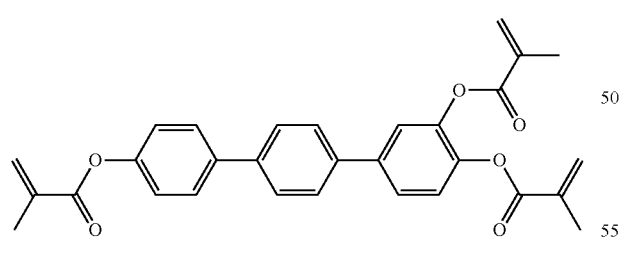

(M316)
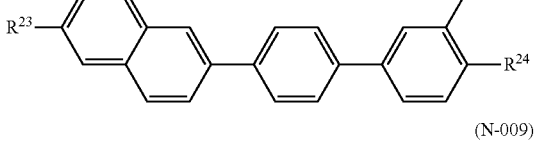

(in the formulae, each of the hydrogen atoms in the phenylene group and naphthalene group may be substituted with —F, —Cl, —CF$_3$, —CH$_3$, or any one of formulae (R-1) to (R-15).

5. The polymerizable compound-containing liquid crystal composition according to claim 1, wherein the compound selected from the group consisting of compounds represented by general formulae (Na), (Nb), or (Nc) is selected from compounds represented by general formulae (N-001) to (N-109), (N-001)
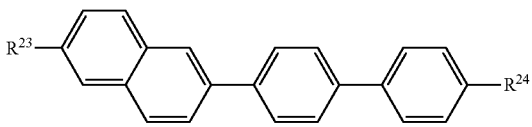

(N-002)
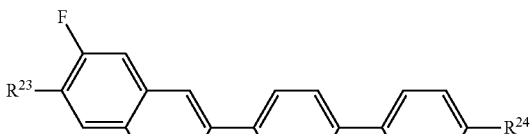

(N-003)

(N-004)
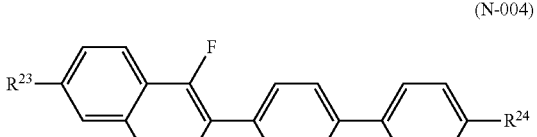

(N-005)

(N-006)
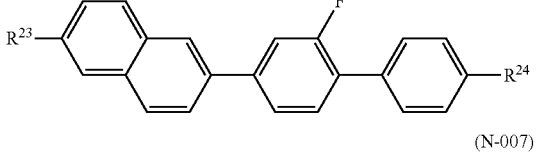

(N-007)
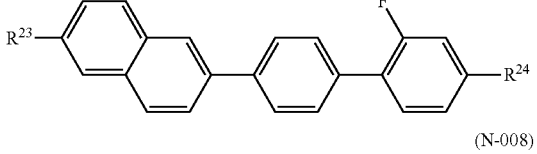

(N-008)
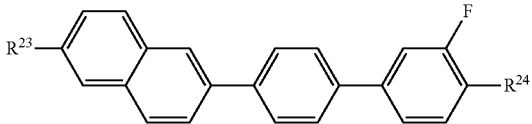

(N-009)
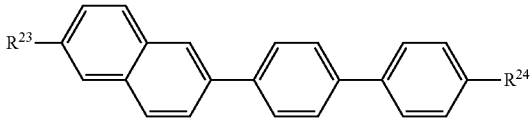

-continued
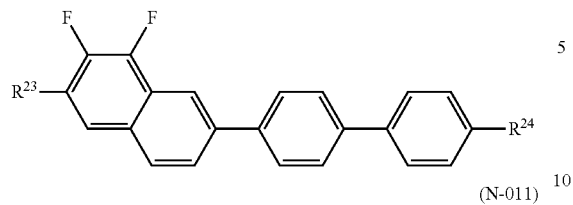
(N-010)
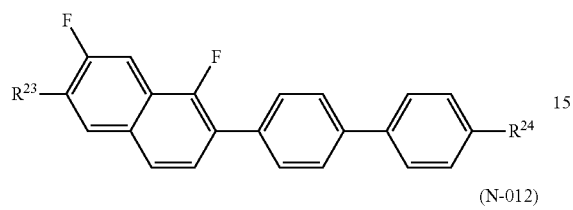
(N-011)
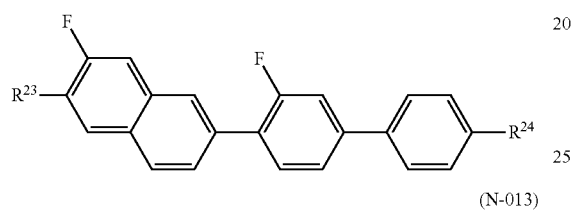
(N-012)
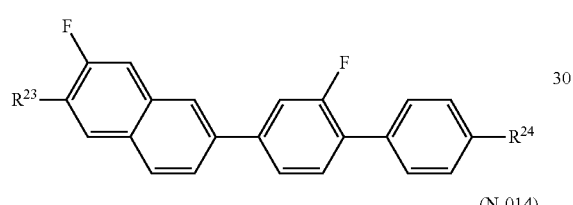
(N-013)
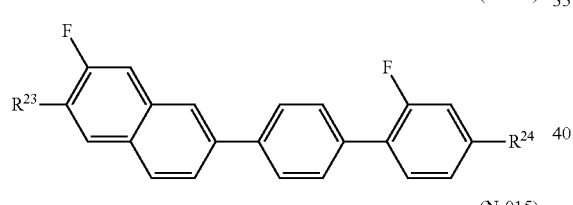
(N-014)
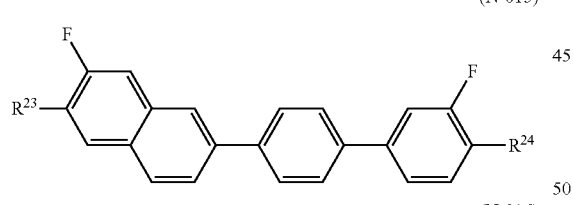
(N-015)
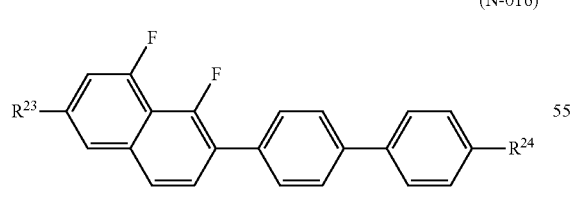
(N-016)
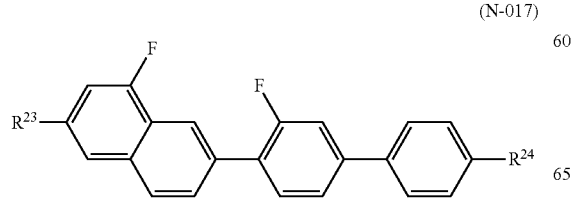
(N-017)
-continued
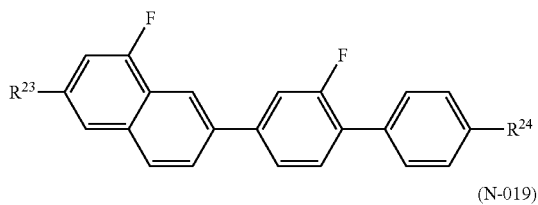
(N-018)
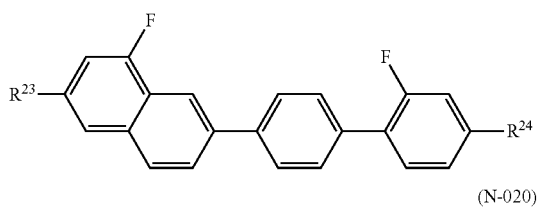
(N-019)
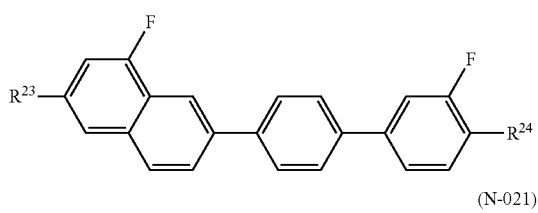
(N-020)
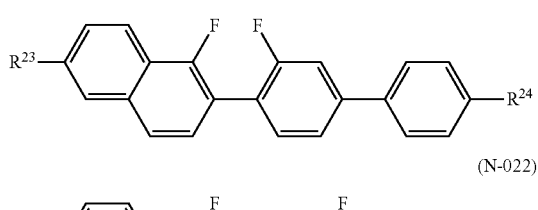
(N-021)
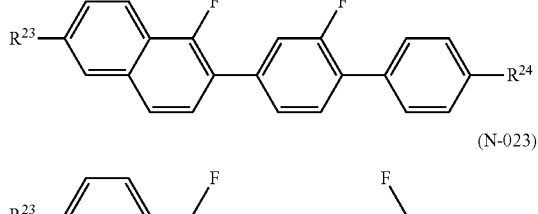
(N-022)
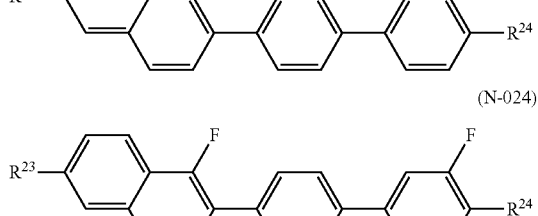
(N-023)
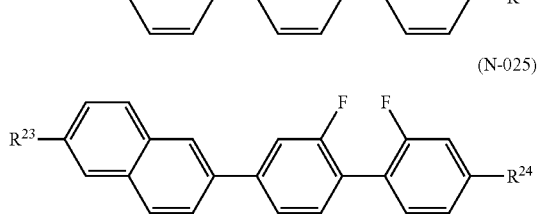
(N-024)
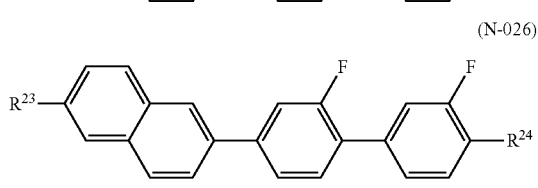
(N-025)
(N-026)

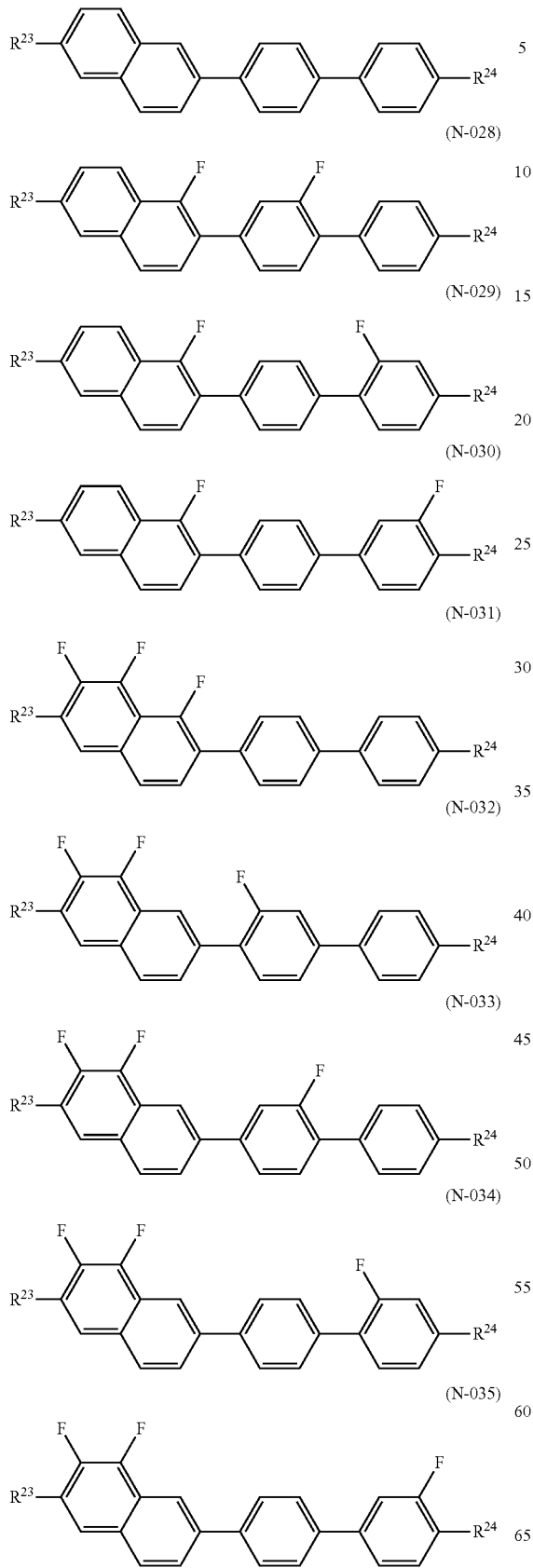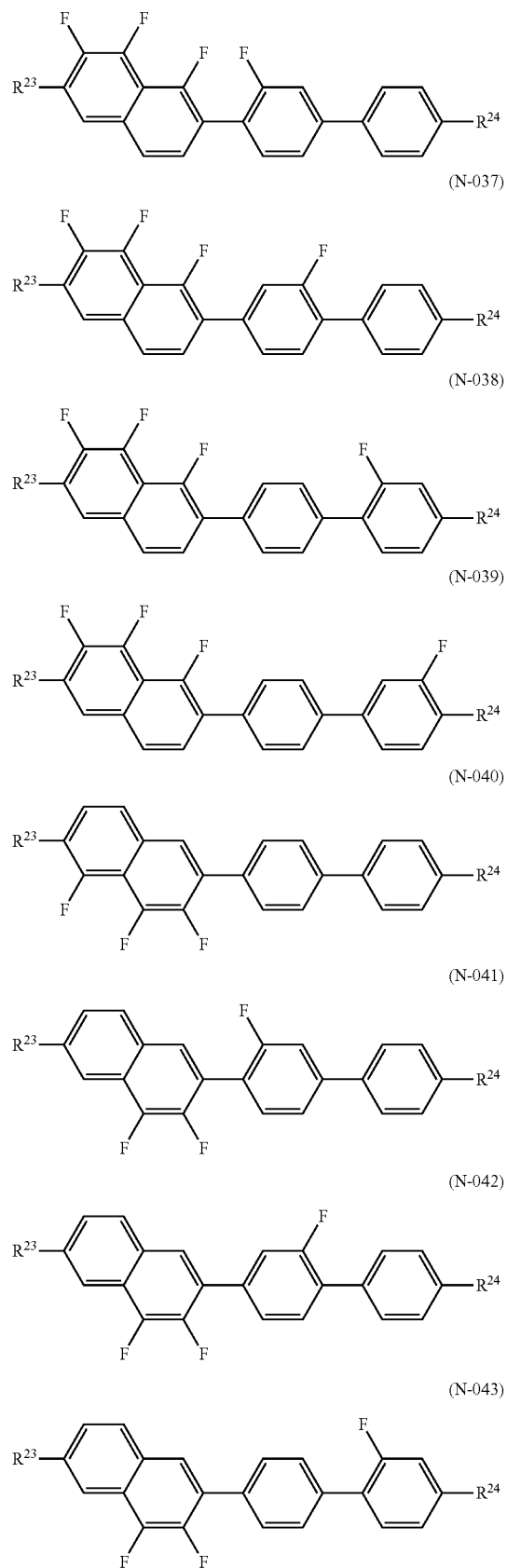

(N-044)
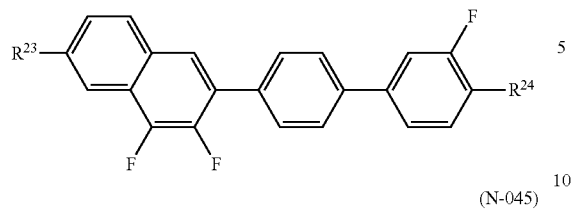
(N-045)
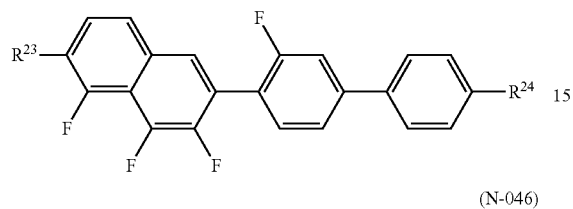
(N-046)
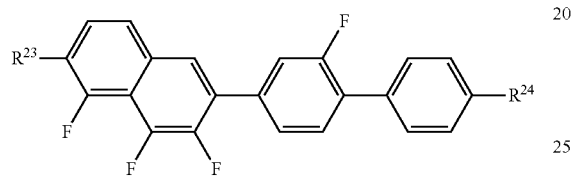
(N-047)
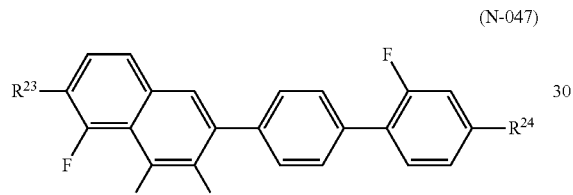
(N-048)
(N-049)
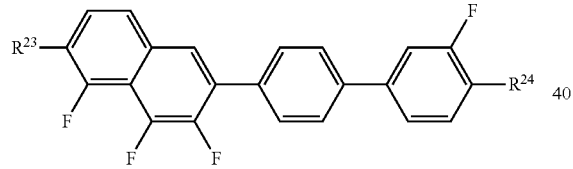
(N-050)
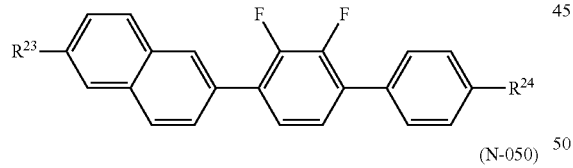
(N-051)
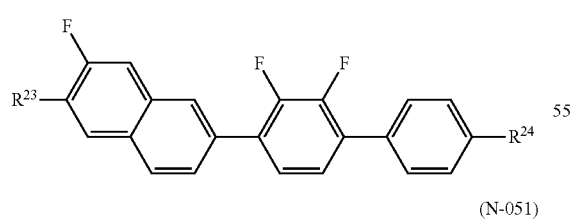
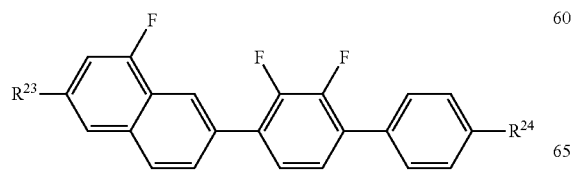
(N-052)
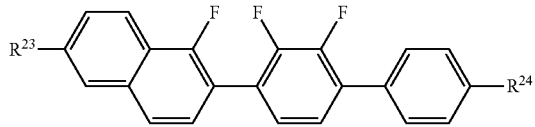
(N-053)
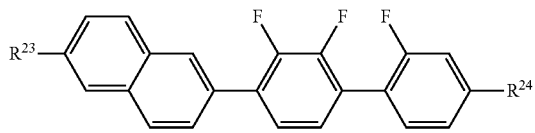
(N-054)
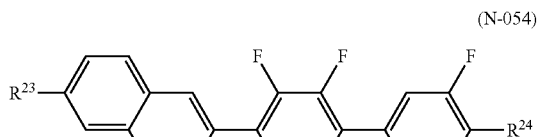
(N-055)
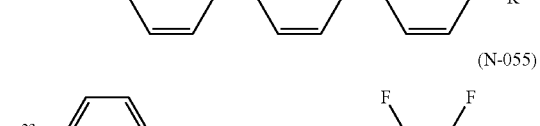
(N-056)
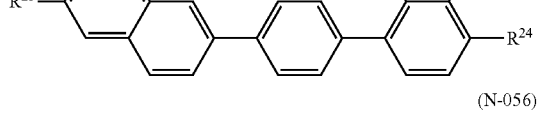
(N-057)
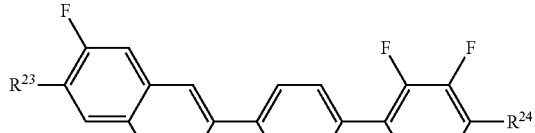
(N-058)
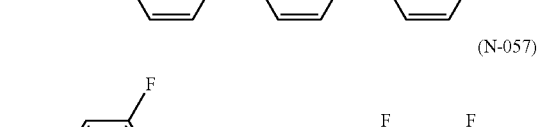
(N-059)
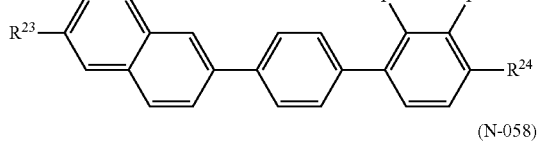
(N-060)
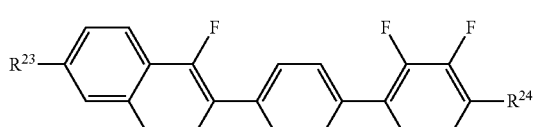
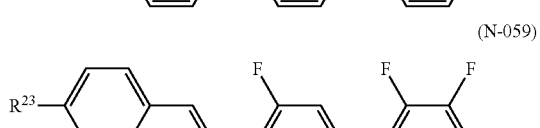
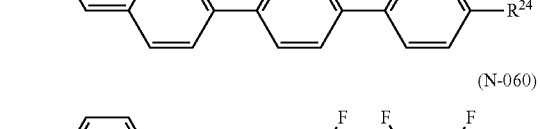
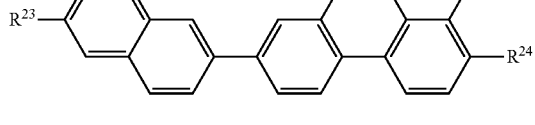

(N-061)
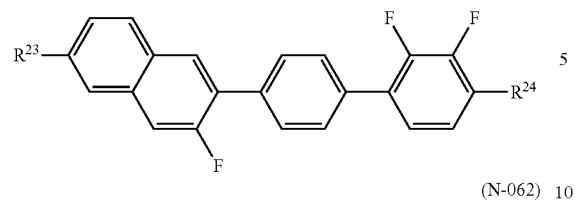
(N-062)
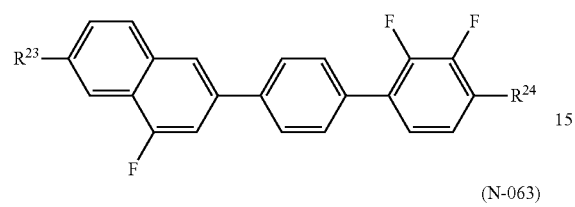
(N-063)
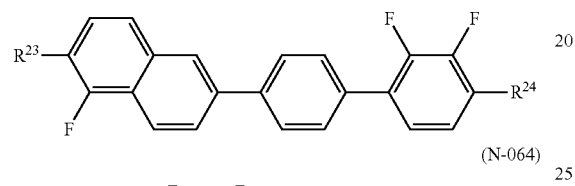
(N-064)
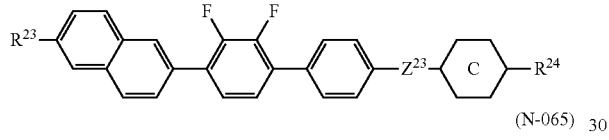
(N-065)
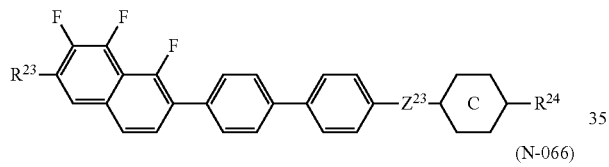
(N-066)
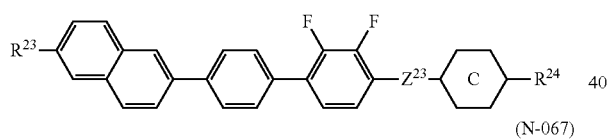
(N-067)
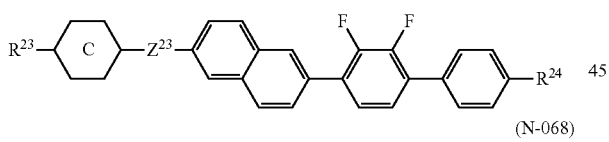
(N-068)
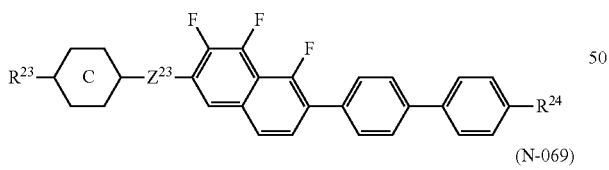
(N-069)
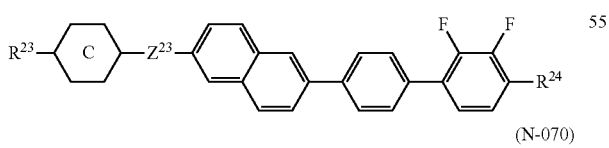
(N-070)
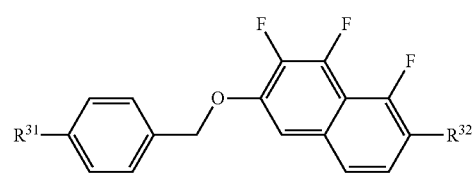
(N-071)
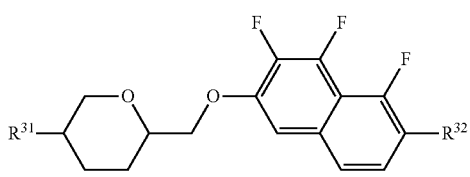
(N-072)
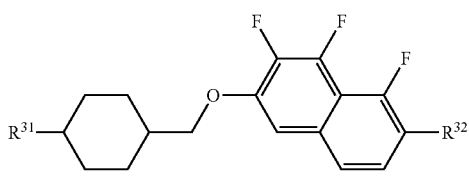
(N-073)
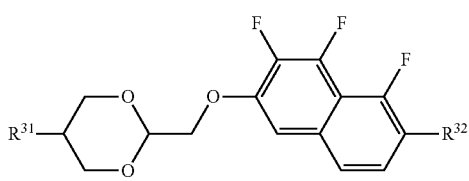
(N-074)
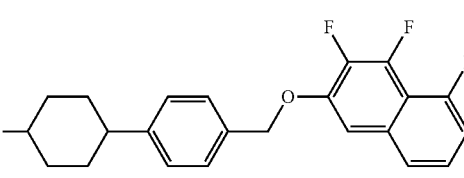
(N-075)
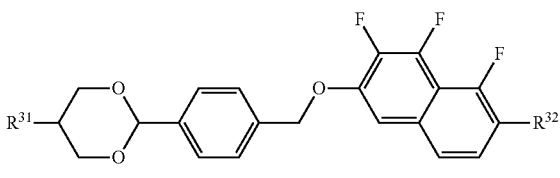
(N-076)
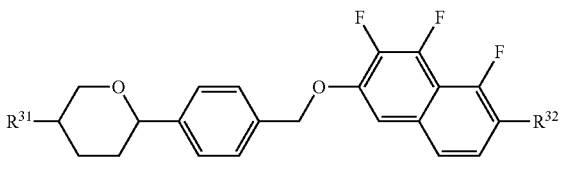
(N-077)
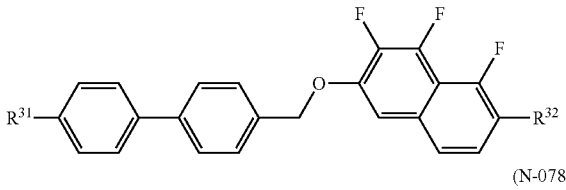
(N-078)
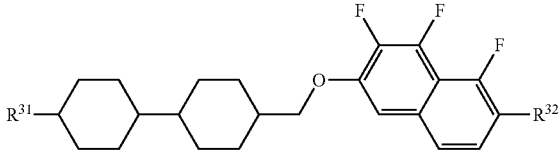

(N-079)
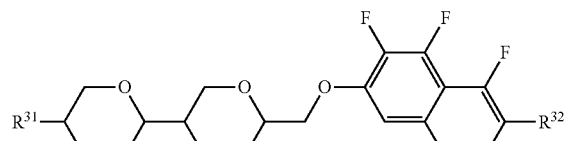
(N-080)
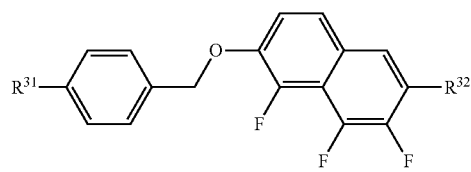
(N-081)
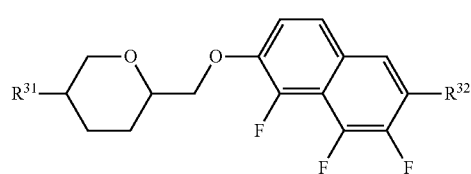
(N-082)
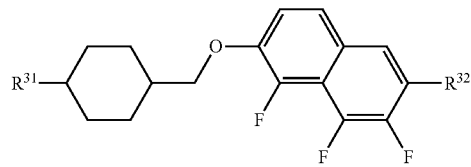
(N-083)
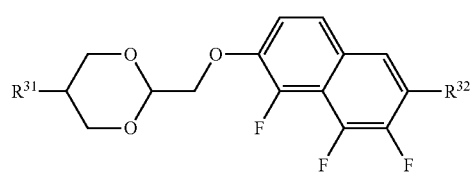
(N-084)
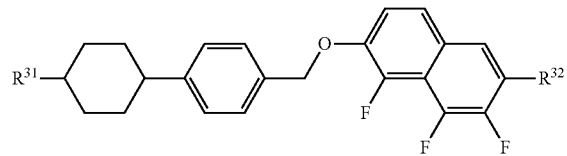
(N-085)
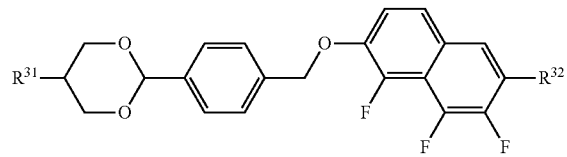
(N-086)
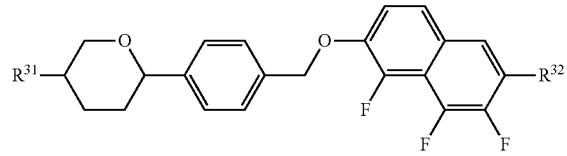
(N-087)
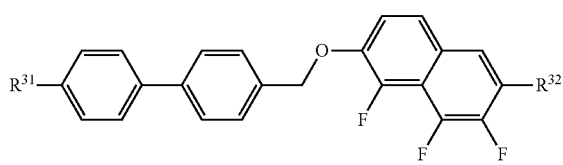
(N-088)
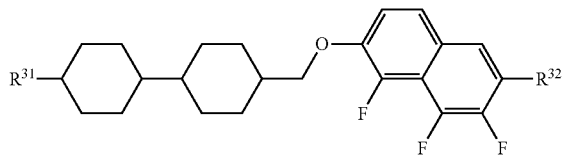
(N-089)
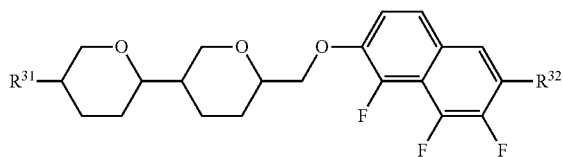
(N-090)
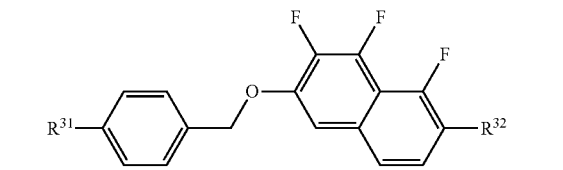
(N-091)
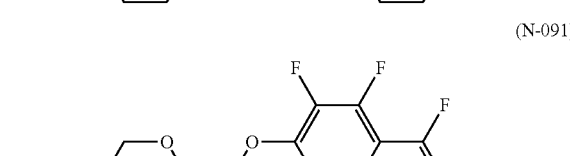
(N-092)
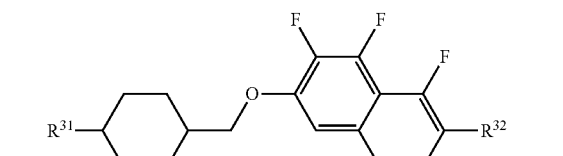
(N-093)
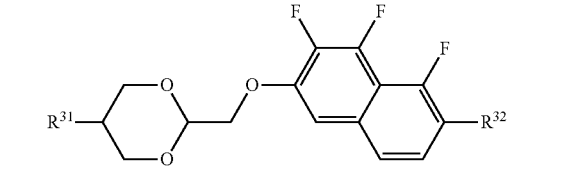
(N-094)
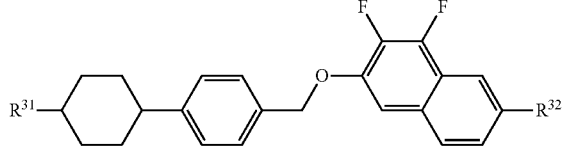

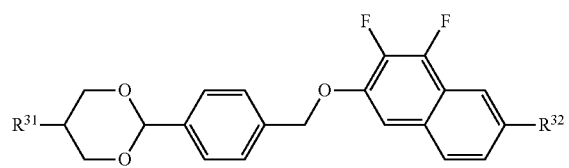
(N-095)

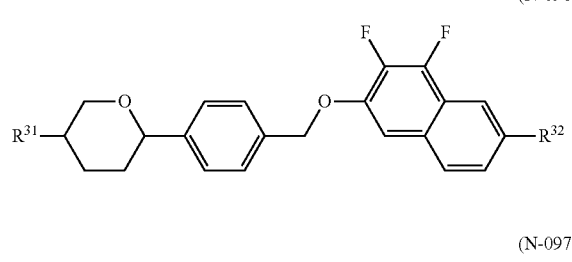
(N-096)
(N-097)

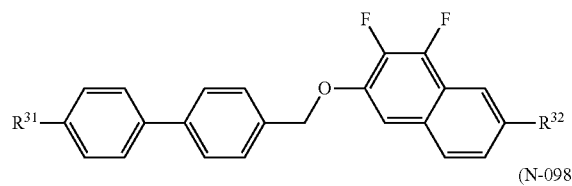
(N-098)

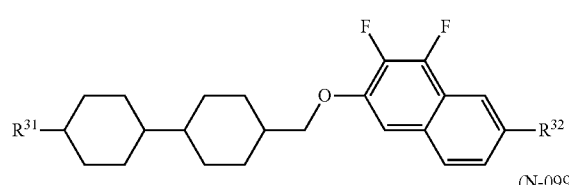
(N-099)

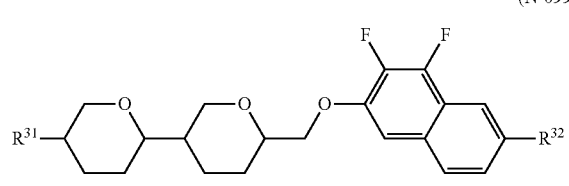
(N-100)

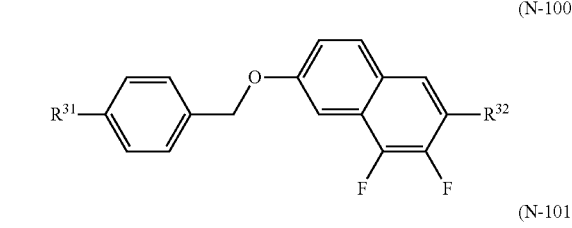
(N-101)

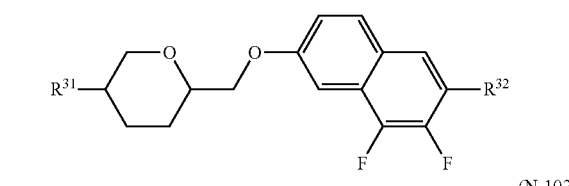
(N-102)

(N-103)
(N-104)
(N-105)
(N-106)
(N-107)
(N-108)
(N-109)

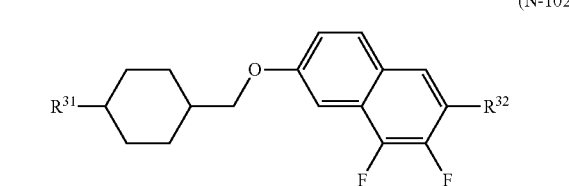

(in the formulae, $R^{23}$ and $R^{31}$ each independently represent the same meaning as $R^{21}$; $R^{24}$ and $R^{32}$ each independently represent the same meaning as $R^{22}$; $Z^{23}$ represents a single bond, —CH₂—O—, —O—CH₂—, —CF₂—O—, —O—CF₂—, —CH₂CH₂—, or —CF₂CF₂—; ring C represents trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group; and each of the hydrogen atoms in the phenylene group and the naphthalene group may be substituted with any of —F, —Cl, —CF$_3$, and —CH$_3$).

6. The polymerizable compound-containing liquid crystal composition according to claim 1, further comprising at least one compounds represented by general formula (II),

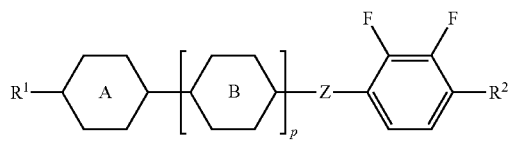

(II)

(in the formula, R$^1$ and R$^2$ each independently represent an alkyl group having 1 to 10 carbon atoms, an alkoxy group having 1 to 10 carbon atoms, an alkenyl group having 2 to 10 carbon atoms, or an alkenyloxy group having 2 to 10 carbon atoms; one —CH$_2$— or two or more non-adjacent —CH$_2$— existing in R$^1$ and R$^2$ each independently may be substituted with —O— and/or —S—; one hydrogen atom or two or more hydrogen atoms existing in R$^1$ and R$^2$ each independently may be substituted with a fluorine atom or a chlorine atom; ring A and ring B represent the same meaning as described above; p represents 0, 1, or 2; and Z represents —OCH$_2$—, —CH$_2$O—, —CF$_2$O—, —OCF$_2$—, —CH$_2$CH$_2$—, —CF$_2$CF$_2$—, or a single bond).

7. The polymerizable compound-containing liquid crystal composition according to claim 6,
wherein the compound represented by general formula (II) is selected from compounds represented by general formulae (II-A1) to (II-A5) and general formulae (II-B1) to (II-B5),

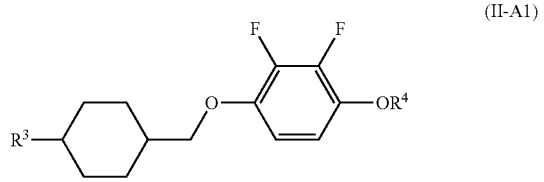
(II-A1)

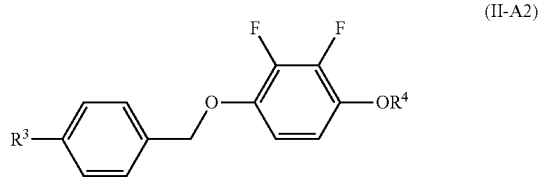
(II-A2)

(II-A3)
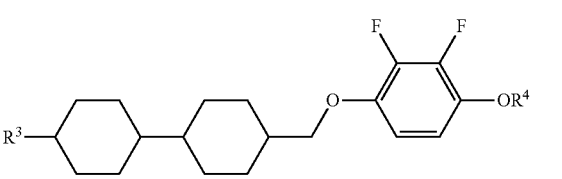

(II-A4)
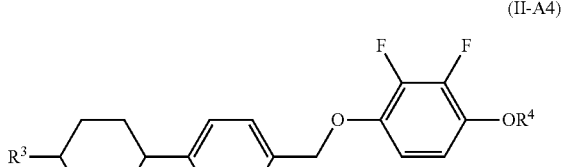

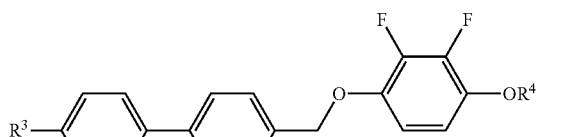
(II-A5)

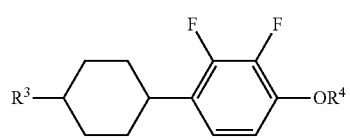
(II-B1)

(II-B2)
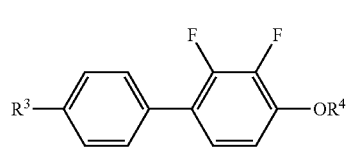

(II-B3)
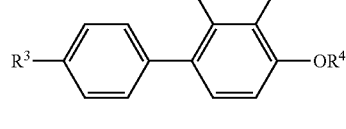

(II-B4)
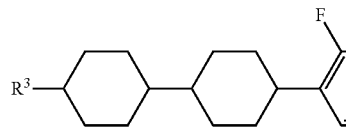

(II-B5)
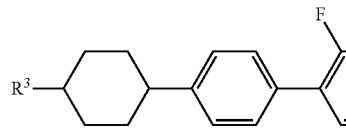

(in the formulae, R$^3$ and R$^4$ each independently represent an alkyl group having 1 to 5 carbon atoms or an alkenyl group having 2 to 5 carbon atoms; and one hydrogen atom or two or more hydrogen atoms existing in R$^3$ and R$^4$ each independently may be substituted with a fluorine atom).

8. The polymerizable compound-containing liquid crystal composition according to claim 1, further comprising at least one compound selected from the group consisting of compounds represented by general formulae (III-A) to (III-J),

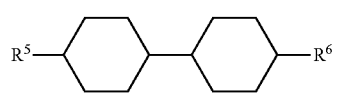
(III-A)

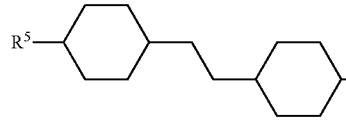
(III-B)

-continued (III-C) R⁵—[cyclohexyl]—CH=CH—[cyclohexyl]—R⁶

(III-D) R⁵—[cyclohexyl]—[phenyl]—R⁶

(III-E) R⁵—[cyclohexyl]—CH₂CH₂—[phenyl]—R⁶

(III-F) R⁵—[phenyl]—[phenyl]—R⁶

(III-G) R⁵—[cyclohexyl]—[cyclohexyl]—[phenyl]—R⁶

(III-H) R⁵—[cyclohexyl]—[phenyl]—[phenyl]—R⁶

(III-I) R⁵—[phenyl]—[phenyl]—[phenyl]—R⁶

(III-J) R⁵—[cyclohexyl]—[phenyl]—[cyclohexyl]—R⁶

(in the formulae, $R^5$ represents an alkyl group having 1 to 5 carbon atoms or an alkenyl group having 2 to 5 carbon atoms; and $R^6$ represents an alkyl group having 1 to 5 carbon atoms, an alkoxy group having 1 to 5 carbon atoms, an alkenyl group having 2 to 5 carbon atoms, or an alkenyloxy group having 2 to 5 carbon atoms).

9. The polymerizable compound-containing liquid crystal composition according to claim 1,
wherein the content of the compound represented by general formula (M) is 0.01 mass % to 2.00 mass %.

10. The polymerizable compound-containing liquid crystal composition according to claim 1,
wherein the content of the compound represented by general formula (Na), (Nb), or (Nc) is 0.5 mass % to 50 mass %.

11. The polymerizable compound-containing liquid crystal composition according to claim 6,
wherein the content of the compound represented by general formula (II) is 10 mass % to 90 mass %.

12. The polymerizable compound-containing liquid crystal composition according to claim 8,
wherein the content of the compounds represented by general formulae (III-A) to (III-J) is 10 mass% to 90 mass%.

13. The polymerizable compound-containing liquid crystal composition according to claim 1,
wherein the liquid crystal composition has a dielectric anisotropy (Δε) of −2.0 to −8.0 at 25° C., a refractive index anisotropy (Δn) of 0.08 to 0.14 at 20° C., a viscosity (η) of 10 mPa·s to 30 mPa·s at 20° C., a rotational viscosity ($γ_1$) of 60 mPa·s to 130 mPa·s at 20° C., and a nematic phase-isotropic liquid phase transition temperature ($T_{ni}$) of 60° C. to 120° C.

14. A compound, represented by general formula (Na), (Na) $R^{21}$—[A—$Z^{21}$]$_m$—[naphthalene with $Y^{21}$, $Y^{22}$, $Y^{23}$]—[$Z^{22}$—B]$_n$—$R^{22}$ (in the formulae, $R^{21}$ and $R^{22}$ each independently represent an alkyl group having 1 to 10 carbon atoms, an alkoxy group having 1 to 10 carbon atoms, an alkenyl group having 2 to 10 carbon atoms, or an alkenyloxy group having 2 to 10 carbon atoms, and one or two or more hydrogen atoms existing in these groups may be substituted with fluorine atoms; $Y^{21}$ to $Y^{23}$ each independently represent a hydrogen atom, a methyl group, a —$CF_3$ group, a fluorine atom, or a chlorine atom; ring A and ring B each independently represent a trans-1,4-cyclohexylene group (one —$CH_2$— or two or more non-adjacent —$CH_2$— in the group may be substituted with —O— or —S—), a 1,4-phenylene group (one —CH= or two or more non-adjacent —CH= in the group may be substituted with —N=), a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group; $Z^{21}$ and $Z^{22}$ each independently represent —$OCH_2$—, —$CH_2O$—, —COO—, —OCO—, —$CF_2O$—, —$OCF_2$—, —$CH_2CH_2$—, —$CF_2CF_2$—, —C≡C—, or a single bond; m represents 0, 1, or 2; when ring A and $Z^{21}$ plurally exist, respectively, they may be different from each other or the same as each other, respectively; n represents 0, 1, or 2; and when ring B and $Z^{22}$ plurally exist, respectively, they may be different from each other or the same as each other, respectively).

15. A liquid crystal display device, which uses the polymerizable compound-containing liquid crystal composition according to claim 1.

16. The liquid crystal display device according to claim 15,
wherein the liquid crystal display device is a liquid crystal display device for active matrix driving.

17. The liquid crystal display device according to claim 15,
wherein the liquid crystal display device is a liquid crystal display device for a PSA mode, a PSVA mode, a VA mode, an IPS mode, or an ECB mode.

18. The liquid crystal display device according to claim 15,
wherein the pretilt angle of the liquid crystal display device is 80° to 89.9°.

19. A compound represented by general formula (Nb)

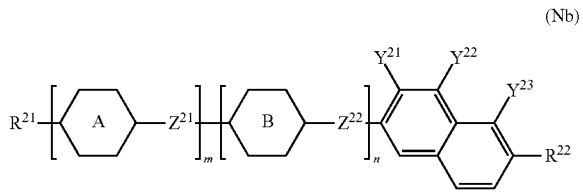

(in the formulae, $R^{21}$ and $R^{22}$ each independently represent an alkyl group having 1 to 10 carbon atoms, an alkoxy group having 1 to 10 carbon atoms, an alkenyl group having 2 to 10 carbon atoms, or an alkenyloxy group having 2 to 10 carbon atoms, and one or two or more hydrogen atoms existing in these groups may be substituted with fluorine atoms; $Y^{21}$ to $Y^{23}$ each independently represent a hydrogen atom, a methyl group, a —$CF_3$ group, a fluorine atom, or a chlorine atom; ring A and ring B each independently represent a trans-1,4-cyclohexylene group (one —$CH_2$— or two or more non-adjacent —$CH_2$— in the group may be substituted with —O— or —S—), a 1,4-phenylene group (one —CH= or two or more non-adjacent —CH= in the group may be substituted with —N=), a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group; $Z^{21}$ and $Z^{22}$ each independently represent —$OCH_2$—, —$CH_2O$—, —COO—, —OCO—, —$CF_2O$—, —$OCF_2$—, —$CH_2CH_2$—, —$CF_2CF_2$—, —C≡C—, or a single bond; m represents 0, 1, or 2; when ring A and $Z^{21}$ plurally exist, respectively, they may be different from each other or the same as each other, respectively; n represents 0, 1, or 2; and when ring B and $Z^{22}$ plurally exist, respectively, they may be different from each other or the same as each other, respectively).

20. A compound represented by general formula (Nc)

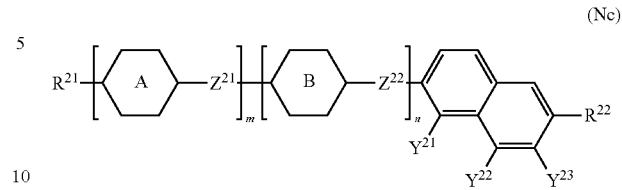

(in the formulae, $R^{21}$ and $R^{22}$ each independently represent an alkyl group having 1 to 10 carbon atoms, an alkoxy group having 1 to 10 carbon atoms, an alkenyl group having 2 to 10 carbon atoms, or an alkenyloxy group having 2 to 10 carbon atoms, and one or two or more hydrogen atoms existing in these groups may be substituted with fluorine atoms; $Y^{21}$ to $Y^{23}$ each independently represent a hydrogen atom, a methyl group, a —$CF_3$ group, a fluorine atom, or a chlorine atom; ring A and ring B each independently represent a trans-1,4-cyclohexylene group (one —$CH_2$— or two or more non-adjacent —$CH_2$— in the group may be substituted with —O— or —S—), a 1,4-phenylene group (one —CH= or two or more non-adjacent —CH= in the group may be substituted with —N=), a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group; $Z^{21}$ and $Z^{22}$ each independently represent —$OCH_2$—, —$CH_2O$—, —COO—, —OCO—, —$CF_2O$—, —$OCF_2$—, —$CH_2CH_2$—, —$CF_2CF_2$—, —C≡C—, or a single bond; m represents 0, 1, or 2; when ring A and $Z^{21}$ plurally exist, respectively, they may be different from each other or the same as each other, respectively; n represents 0, 1, or 2; and when ring B and $Z^{22}$ plurally exist, respectively, they may be different from each other or the same as each other, respectively).

* * * * *